US009650684B2

(12) United States Patent
Dreyfuss et al.

(10) Patent No.: US 9,650,684 B2
(45) Date of Patent: May 16, 2017

(54) METHODS OF IDENTIFYING AND USING GENERAL OR ALTERNATIVE SPLICING INHIBITORS

(75) Inventors: Gideon Dreyfuss, Wynnewood, PA (US); Ihab Younis, Philadelphia, PA (US); Lili Wan, Westfield, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/321,849

(22) PCT Filed: May 21, 2010

(86) PCT No.: PCT/US2010/035803
§ 371 (c)(1),
(2), (4) Date: Mar. 6, 2012

(87) PCT Pub. No.: WO2010/135664
PCT Pub. Date: Nov. 25, 2010

(65) Prior Publication Data
US 2012/0157474 A1 Jun. 21, 2012

Related U.S. Application Data

(60) Provisional application No. 61/180,597, filed on May 22, 2009.

(51) Int. Cl.
C12Q 1/68 (2006.01)
C12Q 1/66 (2006.01)
C12N 15/65 (2006.01)

(52) U.S. Cl.
CPC ................. *C12Q 1/6897* (2013.01)

(58) Field of Classification Search
None
See application file for complete search history.

(56) References Cited

U.S. PATENT DOCUMENTS

| | | | | |
|---|---|---|---|---|
| 5,002,769 A | * | 3/1991 | Friedman | 424/422 |
| 2003/0158140 A1 | | 8/2003 | Schreier et al. | |
| 2003/0202952 A1 | | 10/2003 | Wells et al. | |
| 2007/0248590 A1 | | 10/2007 | Milne et al. | |

OTHER PUBLICATIONS

Wank et al., "Peptide Antibiotics of the Tuberactinomycin Family as Inhibitors of Group I Intron RNA Splicing" 236 Journal of Molecular Biology 1001-1010 (1994).*
Ogihara et al., "p38 MAPK Is Involved in Activin A- and Hepatocyte Growth Factor-mediated Expression of Pro-endocrine Gene Neurogenin 3 in AR42J-B13 Cells" 278(24) The Journal of Biological Chemistry 21693-21700 (2003).*
Groskreutz et al., "Increased Expression and Convenience with the New pGL3 Luciferase Reporter Vectors" 50 Promega Notes Magazine p. 02 (1995).*
Mitsuda et al., "Transcriptional Regulation of the Mouse Presenilin-1 Gene" 272(38) The Journal of Biological Chemistry 23489-23497 (1997).*
Leclerc et al., "Development of a Destabilized Fireflu Luciferase Enzyme for Measurement of Gene Expression" 29 BioTechniques 590-601 (2000).*
O'Reilly et al., "Two Strong 5' Splice Sites and Competing, Suboptimal 3'Splice Sites Involved in Alternative Splicing of Human Immunodeficiency Virus Type 1 RNA" 213 Virology 373-385 (1995).*
Chang et al., "The Nonsense-Mediated Decay RNA Surveillance Pathway" 76 Annual Review of Biochemistry 51-74 (2007).*
Almond et al., "*A rapid fire solution.*" 2004, Promega Notes 87:18-22.
Kaida et al., "*Spliceostatin A targets SF3b and inhibits both splicing and nuclear retention of pre-mRNA.*" 2007, Nat Chem Biol 3(9):576-583.
Kotake et al., "*Splicing factor SF3b as a target of the antitumor natural product pladienolide.*" 2007, Nat Chem Biol 3(9):570-575.
Levinson et al., "*Use of transcriptional synergy to augment sensitivity of a splicing reporter assay,*" 2006, RNA 12(5):925-930.
Lonkar et al., "*Targeted correction of a thalassemia-associated beta-globin mutation induced by pseudo-complementary peptide nucleic acids.*" 2009, Nucleic Acids Res 37(11):3635-44.
Mercure et al., "*Expression of a reporter gene interrupted by the Candida albicans group I intron is inhibited by base analogs.*" 1997, Nucleic Acids Res. 1997, 25(2):431-37.
Michaud et al., "*Sphingosine-1-Phosphate: A Novel Nonhypoxic Activator of hypoxia-Inducible Factor-1 in Vascular Cells.*" 2009, Arterioscler. Thromb. Vasc. Biol. 29:902-08.
Muraki et al., "*Manipulation of alternative splicing by a newly developed inhibitor of Clks.*" 2004, J Biol Chem 279(23):24246-24254.
Pilch et al., "*Specific inhibition of serine- and arginine-rich splicing factors phosphorylation, spliceosome assembly, and splicing by the antitumor drug NB-506.*" 2001, Cancer Res 61(18):6876-6884.
Soret et al., "*Selective modification of alternative splicing by indole derivatives that target serine-arginine-rich protein splicing factors.*" 2005, Proc Natl Acad Sci USA 102(24):8764-8769.
Stoilov et al., "*A high-throughput screening strategy identifies cardiotonic steroids as alternative splicing modulators.*" 2008, Proc Natl Acad Sci USA 105(32):11218-11223.
Sumanasekera et al., "*Substances that can change alternative splice-site selection.*" 2008, Biochem Soc Trans 36(Pt 3):483-490.

\* cited by examiner

Primary Examiner — Nancy J Leith
(74) Attorney, Agent, or Firm — Riverside Law LLP

(57) ABSTRACT

The present invention is based on the discovery of a cell-based system to identify novel modulators of splicing or splicing dependent processes. The cell-based system of the present invention utilizes a fast and highly sensitive reporter, that responds to defects in the splicing machinery itself and is sensitive to changes in the signals that regulate splicing dependent processes such as those that modulate the EJC, splicing-dependent export, localization or translation efficiency. The present invention further uses the cell-based screen to identify several small molecules that modulate both constitutive and alternative splicing. Accordingly, the present invention includes general or alternative splicing inhibitors identified using the assay described herein. The present invention also provides methods of treating a subject having a condition associated with aberrant target RNA expression. The present invention further details a kit that may be directed to specifically detecting a general or alternative splicing inhibitor of the invention.

4 Claims, 12 Drawing Sheets

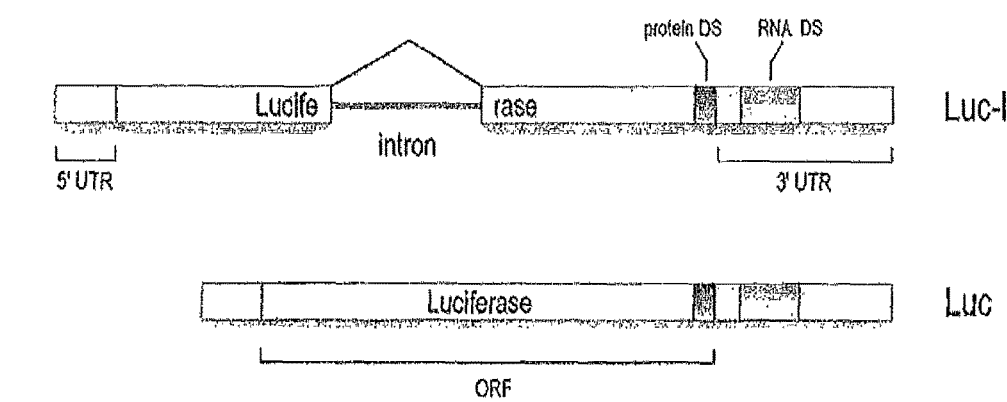
Figure 1A
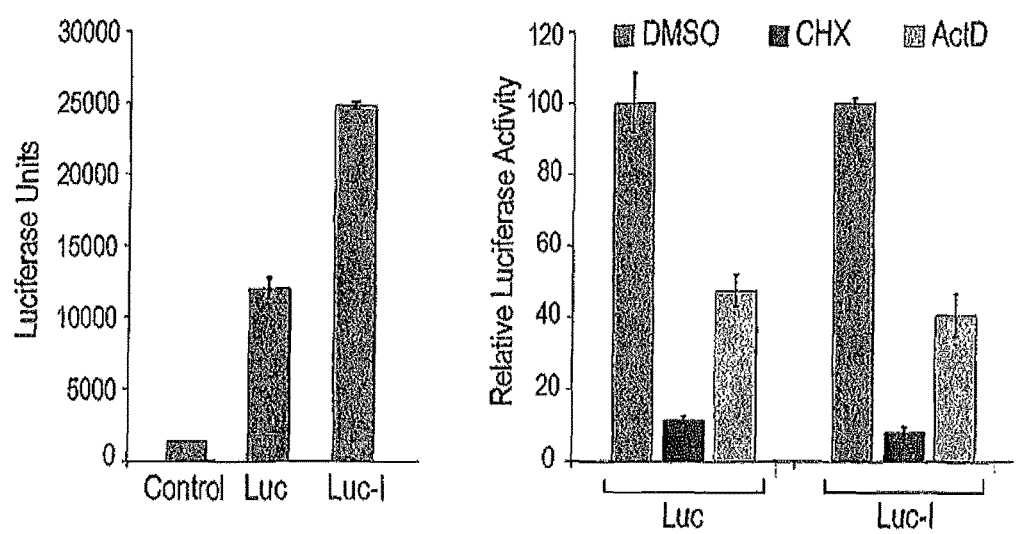
Figure 1B
Figure 1C

Figure 2A
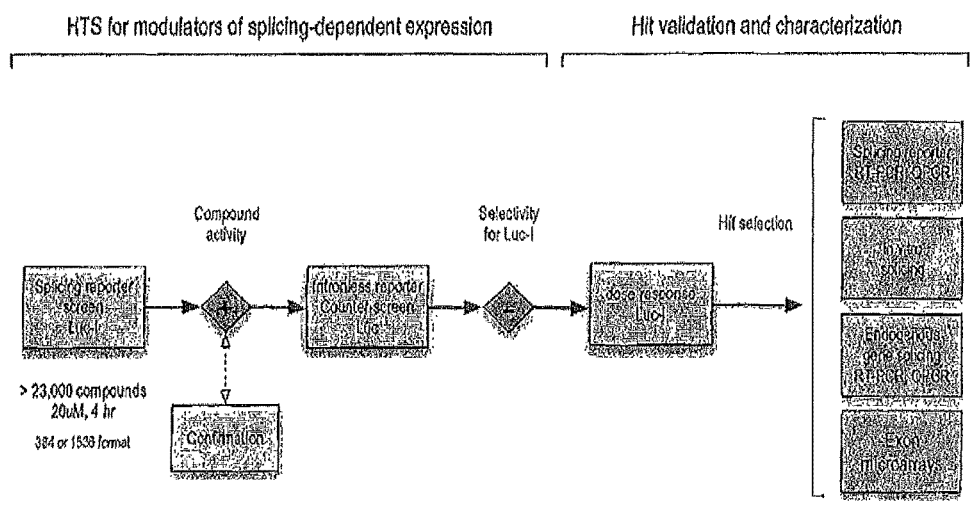
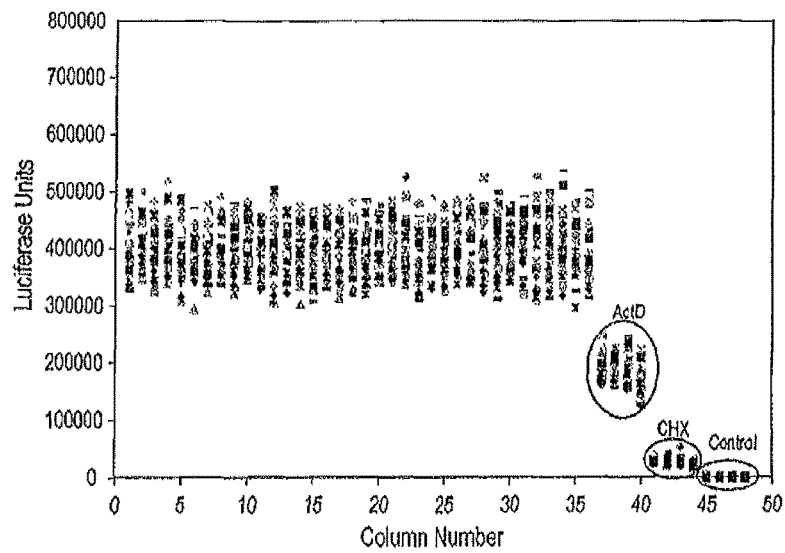
Figure 2B

Clotrimazole
1-[(2-chlorophenyl)-di(phenyl)methyl]imidazole

Flunarizine
1-[bis(4-fluorophenyl)methyl]-4-[(E)-3-phenylprop-2-enyl]piperazine

Chlorhexidine
(1E)-2-[6-[[amino-[[amino-(4-chloroanilino)methylidene]amino]
methylidene]amino]hexyl]-1-[amino-(4-chloroanilino)
methylidene]guanidine

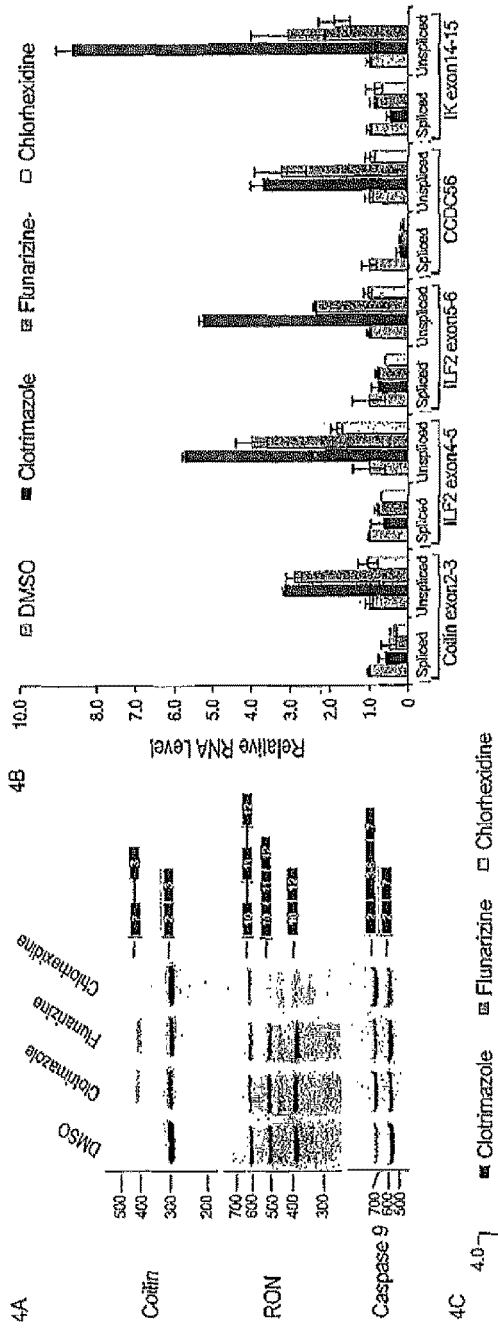
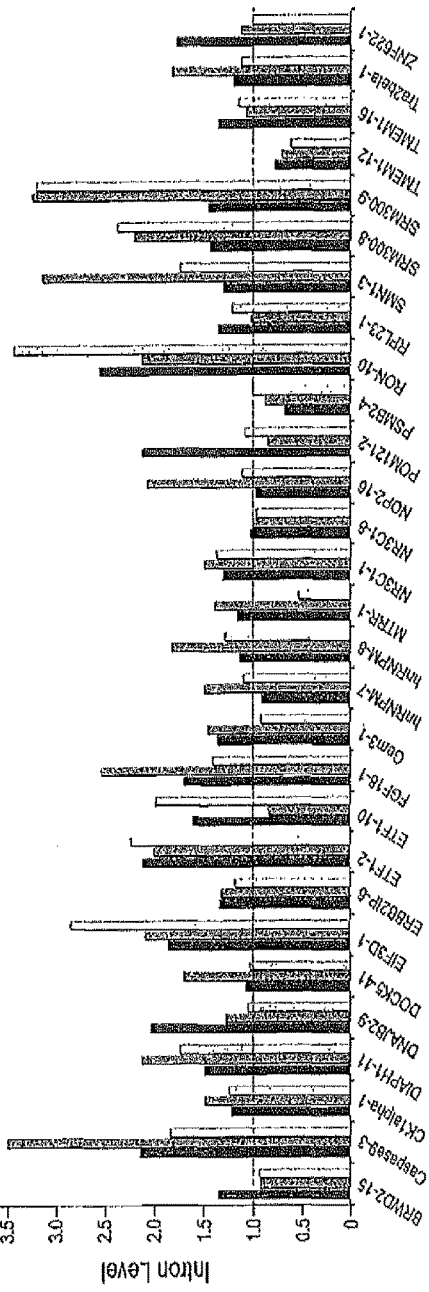
Figure 4A
Figure 4B
Figure 4C

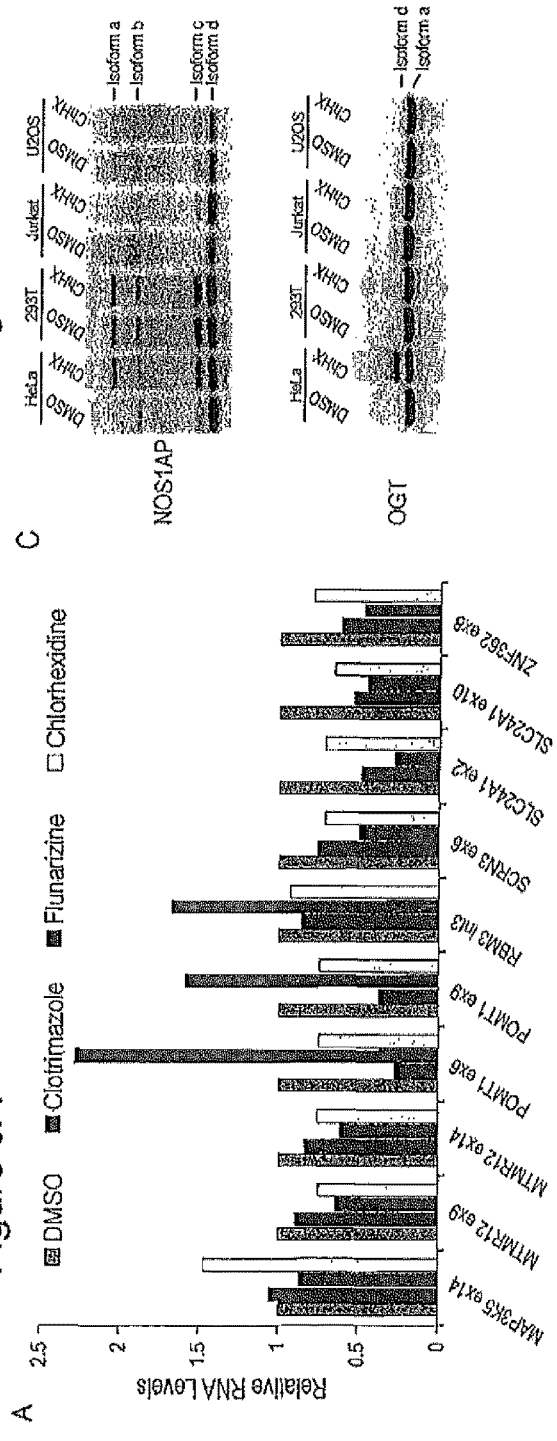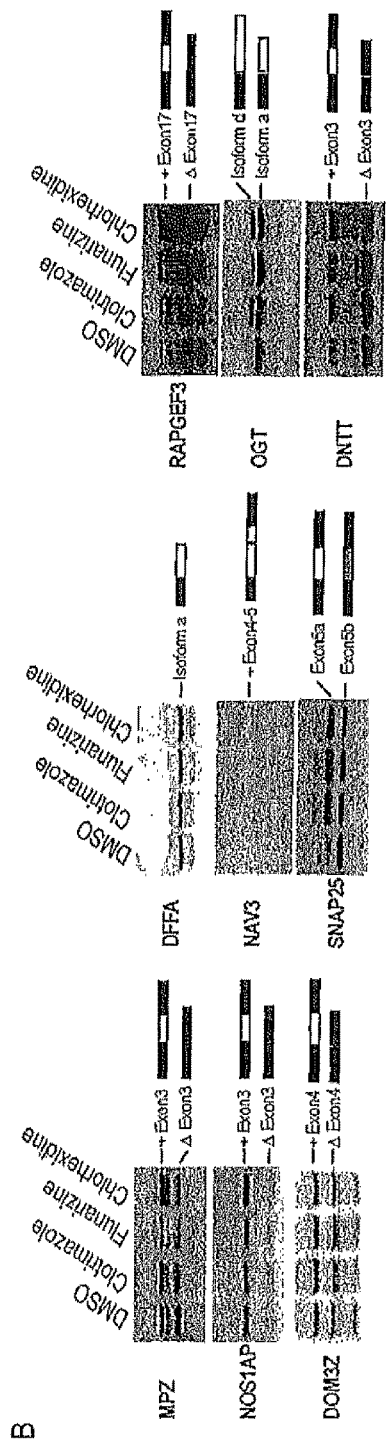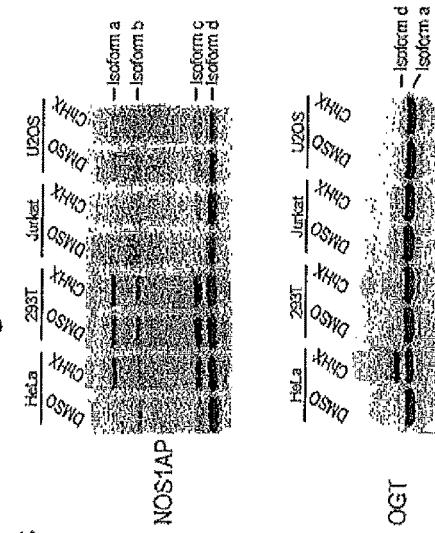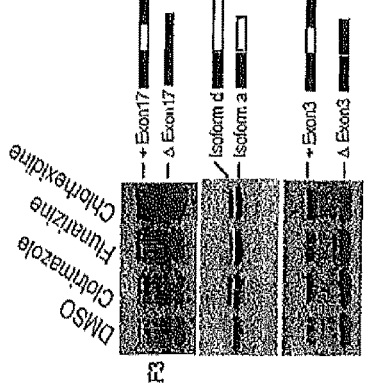
Figure 9A
Figure 9B
Figure 9C

| Compound | Splicing Activity % of control (Luc-I/Luc) | Structure |
|---|---|---|
| MELIACIN-1(2),14(15)-DIEN-3,7-DIONE | 83 | 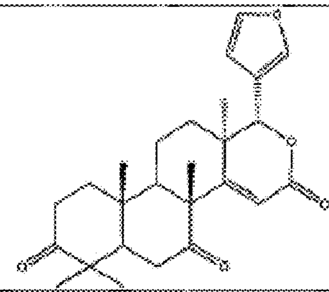 |
| M10H10 | 86 | 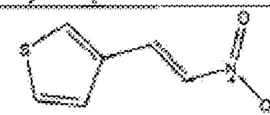 |
| GBLD | 73 | 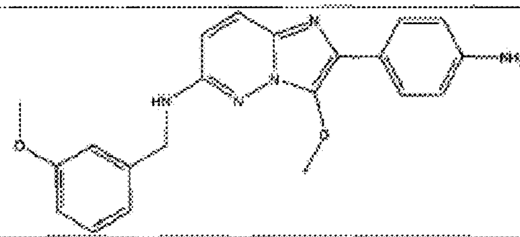 |
| Chem2A7 | 69 | 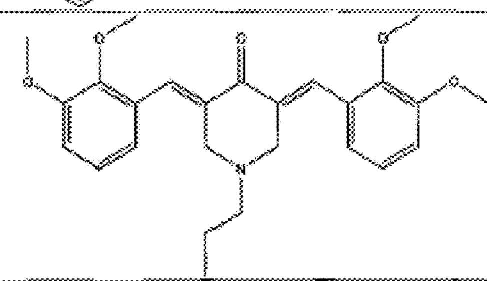 |
| Thymoquinone | 76 | 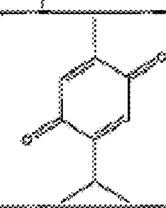 |
| Quercitin | 81 | 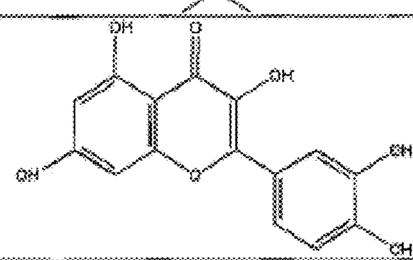 |

Figure 11-1

| Compound | Splicing Activity % of control (Luc-I/Luc) | Structure |
| --- | --- | --- |
| Emicymarin | 57 | 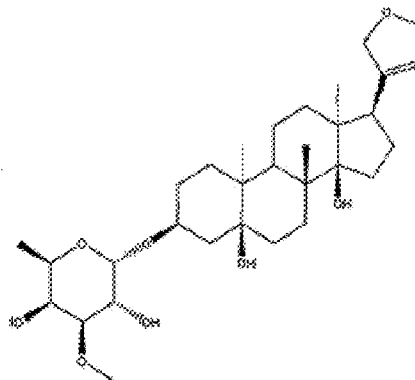 |
| Strophanthidin | 51 | 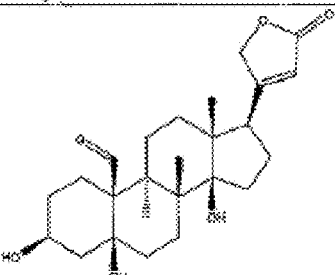 |
| H-7 | 83 | 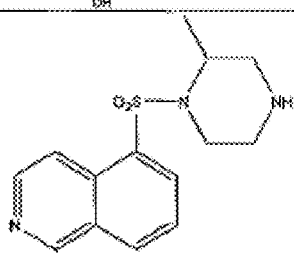 |
| Isradipine | 70 | 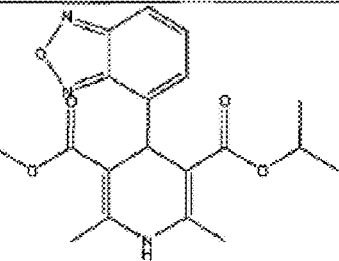 |
Figure 11-2

SEQUENCE LISTING

```
<160> NUMBER OF SEQ ID NOS: 74

<210> SEQ ID NO 1
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 1
gctcaaatgg tggtggacag g                                        21

<210> SEQ ID NO 2
<211> LENGTH: 25
<212> TYPE: DNA
<213> ORGANISM: Artificial Sequence
<220> FEATURE:
<223> OTHER INFORMATION: RT-PCR Primer

<400> SEQUENCE: 2
gcagctgcta acagtggtaa cagac                                    25

<210> SEQ ID NO 3
<211> LENGTH: 17
<212> TYPE: DNA
<213> ORGANISM: Artificial Sequence
<220> FEATURE:
<223> OTHER INFORMATION: RT-PCR Primer

<400> SEQUENCE: 3
tgtgagaggc agcttcc                                             17

<210> SEQ ID NO 4
<211> LENGTH: 17
<212> TYPE: DNA
```

```
<213> ORGANISM: Artificial Sequence
<220> FEATURE:
<223> OTHER INFORMATION: RT-PCR Primer

<400> SEQUENCE: 4
tagctgcttc ctccgcc                                                    17

<210> SEQ ID NO 5
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 5
gctcttcctt tgttcatctc c                                               21

<210> SEQ ID NO 6
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 6
catctggctc ggggttactg c                                               21

<210> SEQ ID NO 7
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 7
tgtgtggagt tcatgtcatg ga                                              22

<210> SEQ ID NO 8
<211> LENGTH: 25
<212> TYPE: DNA
<213> ORGANISM: Artificial Sequence
<220> FEATURE:
<223> OTHER INFORMATION: RT-PCR Primer

<400> SEQUENCE: 8
tgggtgtctc tactggattc tgaaa                                           25

<210> SEQ ID NO 9
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 9
cctggtgttg gctatttgta tcc                                             23

<210> SEQ ID NO 10
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 10
gccctcttgc acactctgtt c                                               21
```

<210> SEQ ID NO 11
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 11
aggccttgct gaagaggaat c                                              21

<210> SEQ ID NO 12
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 12
gacatttctg gaagacagcc aaa                                            23

<210> SEQ ID NO 13
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 13
gattgtggct ccagggacat                                                20

<210> SEQ ID NO 14
<211> LENGTH: 25
<212> TYPE: DNA
<213> ORGANISM: Artificial Sequence
<220> FEATURE:
<223> OTHER INFORMATION: RT-PCR Primer

<400> SEQUENCE: 14
aagctgccct ttcctaaaac taaat                                          25

<210> SEQ ID NO 15
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 15
gggaaggcac agaatcatat cc                                             22

<210> SEQ ID NO 16
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 16
aaattcagcg taaagggaa gga                                             23

<210> SEQ ID NO 17
<211> LENGTH: 20
<212> TYPE: DNA
<213> ORGANISM: Artificial Sequence
<220> FEATURE:

<223> OTHER INFORMATION: RT-PCR Primer

<400> SEQUENCE: 17
ccctgatccc tgtgtggaat                                          20

<210> SEQ ID NO 18
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 18
gacacataag cctgatgctc tgtt                                     24

<210> SEQ ID NO 19
<211> LENGTH: 19
<212> TYPE: DNA
<213> ORGANISM: Artificial Sequence
<220> FEATURE:
<223> OTHER INFORMATION: RT-PCR Primer

<400> SEQUENCE: 19
cgaacctcgt ccgctgtct                                           19

<210> SEQ ID NO 20
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 20 gttccccaa cctttctatc g                                         21

<210> SEQ ID NO 21
<211> LENGTH: 28
<212> TYPE: DNA
<213> ORGANISM: Artificial Sequence
<220> FEATURE:
<223> OTHER INFORMATION: RT-PCR Primer

<400> SEQUENCE: 21
gagactcgtt gtcttggtat tatgatgt                                 28

<210> SEQ ID NO 22
<211> LENGTH: 16
<212> TYPE: DNA
<213> ORGANISM: Artificial Sequence
<220> FEATURE:
<223> OTHER INFORMATION: RT-PCR Primer

<400> SEQUENCE: 22
gcagcagccc gcaaag                                              16

<210> SEQ ID NO 23
<211> LENGTH: 27
<212> TYPE: DNA
<213> ORGANISM: Artificial Sequence
<220> FEATURE:
<223> OTHER INFORMATION: RT-PCR Primer

<400> SEQUENCE: 23
ttatttgccc cttatacaaa cttagct                                  27

```
<210> SEQ ID NO 24
<211> LENGTH: 26
<212> TYPE: DNA
<213> ORGANISM: Artificial Sequence
<220> FEATURE:
<223> OTHER INFORMATION: RT-PCR Primer

<400> SEQUENCE: 24
tgtctcacat accaagagcc atattt                                          26

<210> SEQ ID NO 25
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 25
gcttccggtg aggtgcttat t                                               21

<210> SEQ ID NO 26
<211> LENGTH: 17
<212> TYPE: DNA
<213> ORGANISM: Artificial Sequence
<220> FEATURE:
<223> OTHER INFORMATION: RT-PCR Primer

<400> SEQUENCE: 26
tgcacctgct gcgtcaa                                                    17

<210> SEQ ID NO 27
<211> LENGTH: 16
<212> TYPE: DNA
<213> ORGANISM: Artificial Sequence
<220> FEATURE:
<223> OTHER INFORMATION: RT-PCR Primer

<400> SEQUENCE: 27
cgcatggccg gatgag                                                     16

<210> SEQ ID NO 28
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 28
agatccagaa ggcgggagtt                                                 20

<210> SEQ ID NO 29
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 29
ctgactcttc gactgcgtgt ct                                              22

<210> SEQ ID NO 30
<211> LENGTH: 21
<212> TYPE: DNA
<213> ORGANISM: Artificial Sequence
<220> FEATURE:
<223> OTHER INFORMATION: RT-PCR Primer
```

<400> SEQUENCE: 30
gtaaacacct gcgggaaaca g                                      21

<210> SEQ ID NO 31
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 31
ggcgtgttct catacgtttt tg                                     22

<210> SEQ ID NO 32
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 32
gggtctcctg agattcccct agt                                    23

<210> SEQ ID NO 33
<211> LENGTH: 25
<212> TYPE: DNA
<213> ORGANISM: Artificial Sequence
<220> FEATURE:
<223> OTHER INFORMATION: RT-PCR Primer

<400> SEQUENCE: 33
cgtggaatag gcactgttac ttttg                                  25

<210> SEQ ID NO 34
<211> LENGTH: 27
<212> TYPE: DNA
<213> ORGANISM: Artificial Sequence
<220> FEATURE:
<223> OTHER INFORMATION: RT-PCR Primer

<400> SEQUENCE: 34
attcctgcag aaggatacat atagctt                                27

<210> SEQ ID NO 35
<211> LENGTH: 26
<212> TYPE: DNA
<213> ORGANISM: Artificial Sequence
<220> FEATURE:
<223> OTHER INFORMATION: RT-PCR Primer

<400> SEQUENCE: 35
cacgtcaaga tggtaagtca gtagga                                 26

<210> SEQ ID NO 36
<211> LENGTH: 29
<212> TYPE: DNA
<213> ORGANISM: Artificial Sequence
<220> FEATURE:
<223> OTHER INFORMATION: RT-PCR Primer

<400> SEQUENCE: 36
caacatactg caccctattt aacttagac                              29

<210> SEQ ID NO 37
<211> LENGTH: 21

<212> TYPE: DNA
<213> ORGANISM: Artificial Sequence
<220> FEATURE:
<223> OTHER INFORMATION: RT-PCR Primer

<400> SEQUENCE: 37
tcgagccgat catctgattt c                                            21

<210> SEQ ID NO 38
<211> LENGTH: 27
<212> TYPE: DNA
<213> ORGANISM: Artificial Sequence
<220> FEATURE:
<223> OTHER INFORMATION: RT-PCR Primer

<400> SEQUENCE: 38
tcaaattaag gagagtgtac gaatgaa                                      27

<210> SEQ ID NO 39
<211> LENGTH: 19
<212> TYPE: DNA
<213> ORGANISM: Artificial Sequence
<220> FEATURE:
<223> OTHER INFORMATION: RT-PCR Primer

<400> SEQUENCE: 39
cagtgagcgg caggatgaa                                               19

<210> SEQ ID NO 40
<211> LENGTH: 18
<212> TYPE: DNA
<213> ORGANISM: Artificial Sequence
<220> FEATURE:
<223> OTHER INFORMATION: RT-PCR Primer

<400> SEQUENCE: 40
tgcacagctg agggcaaa                                                18

<210> SEQ ID NO 41
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 41
tgctaaagca atgcagtgaa ca                                           22

<210> SEQ ID NO 42
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 42
gcaagaaccc tgtgagcaag a                                            21

<210> SEQ ID NO 43
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 43
tggtcagcca gatggtctga                                              20

<210> SEQ ID NO 44
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 44
agggtcaagt ggctggtagg t                                            21

<210> SEQ ID NO 45
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 45
tctgaatgct ctcagttgaa tgg                                          23

<210> SEQ ID NO 46
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 46
tgcccacaag gaattaaatg g                                            21

<210> SEQ ID NO 47
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 47
tttcctcccc ttgcctaagt g                                            21

<210> SEQ ID NO 48
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 48
agcacaaaag catccctgtg t                                            21

<210> SEQ ID NO 49
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 49
gactggatta ggccctggtt t                                            21

<210> SEQ ID NO 50
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 50
gcaattactc ctgcaaggca ta                                       22

<210> SEQ ID NO 51
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 51
aaatgatgag ggaaggtggt ttag                                     24

<210> SEQ ID NO 52
<211> LENGTH: 19
<212> TYPE: DNA
<213> ORGANISM: Artificial Sequence
<220> FEATURE:
<223> OTHER INFORMATION: RT-PCR Primer

<400> SEQUENCE: 52
ccaaacctgc tggccagat                                           19

<210> SEQ ID NO 53
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 53
ccaccttagt gggagggagt t                                        21

<210> SEQ ID NO 54
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 54
ctcacgtatc cctcaaccct tt                                       22

<210> SEQ ID NO 55
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 55
tgcacagacc attcggaaga                                          20

<210> SEQ ID NO 56
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 56
tgctttagcc tgtcagctcc ta                                       22

<210> SEQ ID NO 57
<211> LENGTH: 19
<212> TYPE: DNA
<213> ORGANISM: Artificial Sequence
<220> FEATURE:
<223> OTHER INFORMATION: RT-PCR Primer

<400> SEQUENCE: 57
ccgccagacc gtagtctca                                            19

<210> SEQ ID NO 58
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 58
agacatgatg ctaatggcac aaa                                       23

<210> SEQ ID NO 59
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 59
aatgcggaga agatgaccag tac                                       23

<210> SEQ ID NO 60
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 60
cccggaaagg atacactgct t                                         21

<210> SEQ ID NO 61
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 61
cctctccgct ccagctacct                                           20

<210> SEQ ID NO 62
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 62
tgcttgcgct cctcttcagt                                           20

<210> SEQ ID NO 63
<211> LENGTH: 19
<212> TYPE: DNA
<213> ORGANISM: Artificial Sequence
<220> FEATURE:
<223> OTHER INFORMATION: RT-PCR Primer

```
<400> SEQUENCE: 63
ccgaagccat gctcatcct                                              19

<210> SEQ ID NO 64
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 64
cacctcacct ctcgtgttgg a                                           21

<210> SEQ ID NO 65
<211> LENGTH: 18
<212> TYPE: DNA
<213> ORGANISM: Artificial Sequence
<220> FEATURE:
<223> OTHER INFORMATION: RT-PCR Primer

<400> SEQUENCE: 65
ggagagcccg ggtttacg                                               18

<210> SEQ ID NO 66
<211> LENGTH: 26
<212> TYPE: DNA
<213> ORGANISM: Artificial Sequence
<220> FEATURE:
<223> OTHER INFORMATION: RT-PCR Primer

<400> SEQUENCE: 66
gcagaagttc acattgttga taatga                                      26

<210> SEQ ID NO 67
<211> LENGTH: 21
<212> TYPE: DNA
<213> ORGANISM: Artificial Sequence
<220> FEATURE:
<223> OTHER INFORMATION: RT-PCR Primer

<400> SEQUENCE: 67
cacccagtgc caacctagtt c                                           21

<210> SEQ ID NO 68
<211> LENGTH: 26
<212> TYPE: DNA
<213> ORGANISM: Artificial Sequence
<220> FEATURE:
<223> OTHER INFORMATION: RT-PCR Primer

<400> SEQUENCE: 68
ccctatccct tacacttacc tcaaac                                      26

<210> SEQ ID NO 69
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 69
cgagatgata gtttgccctc ttc                                         23

<210> SEQ ID NO 70
```

```
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 70
tccccaactt tccactacaa aag                                             23

<210> SEQ ID NO 71
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 71
gagcgggtgg aagtggagga ggat                                            24

<210> SEQ ID NO 72
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 72
tcagaggatg aggcagcgag aggc                                            24

<210> SEQ ID NO 73
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 73
ggtagagtta gagcccgtgc ggag                                            24

<210> SEQ ID NO 74
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 74
ggcctccctc cttcacgacc aaag                                            24
```

METHODS OF IDENTIFYING AND USING GENERAL OR ALTERNATIVE SPLICING INHIBITORS

CROSS-REFERENCE TO RELATED APPLICATION

This application is the U.S. national phase application filed under 35 U.S.C. §371 claiming benefit to International Patent Application No, PCT/US2010/35803, filed on May 21, 2010, which is entitled to priority under 35 U.S.C. §119(e) to U.S. Provisional Patent Application No. 61/180,597, filed on May 22, 2009, each of which application is hereby incorporated herein by reference in its entirety.

BACKGROUND OF THE INVENTION

Extensive posttranscriptional processing is required before eukaryotic pre-mRNA matures and exits from the nucleus to the cytoplasm, including the addition of a 7-methylguanosine cap at the 5' end, the cleavage and addition of a poly-A tail at the 3' end as well as the removal of intervening sequences or introns by the spliceosome. The vast majority of higher eukaryotic genes contain multiple introns that need to be spliced out with high precision and fidelity in order to maintain the reading frame of the exons. Splicing of pre-mRNA depends on the recognition of short consensus sequences at the boundaries and within introns by an array of small nuclear ribonucleoprotein (snRNP) complexes (consisting of snRNPs U1, U2, U4, U5, U6, U11, U12m U4atc and U6atc) and a large number of proteins, including spliceosomal proteins and positively as well as negatively acting splicing modulators (Black, 2003, Annu Rev Biochem 72:291-336; Faustino et al., 2003, Genes Dev 17:419-437; Graveley, 2006, RNA 6:1197-1211). Serine-arginine-rich (SR)-domain-containing proteins (Manley et al., 1996, Genes Dev 10:1569-1579) generally serve to promote constitutive splicing. They also modulate alternative splicing by binding to intronic or exonic splicing enhancer (ISE or ESE, respectively) sequences (Graveley, 2000, RNA 6:1197-1211; Black, 2003, Annu Rev Biochem 72:291-336). Other pre-mRNA binding proteins that lack SR domains, such as hnRNPs, regulate splicing by binding to intronic or exonic splicing suppressor (ISS or ESS, respectively) sites and also act as general splicing modulators (Dreyfuss et al., 2002, Nat Rev Mol Cell Biol 3:195-205; Wang and Burge et al., 2008, RNA 14:802-813).

The SR protein family is a class of at least 10 proteins that have a characteristic serine/arginine rich domain in addition to an RNA-binding region (Bourgeois et al., 2004, frog Nucleic Acid Res Mol Biol 78:37-88). SR proteins are generally thought to enhance splicing by simultaneously binding to U170K, a core component of the U1 snRNP, at the 5' splice site, and the U2AF35 at the 3' splice site, thus bridging the two ends of the intron (Jamison et al., 1995, Nucleic Acids Res 23:3260-3267; Katz et al., 1994, Nature 368:119-124). While this particular function of SR proteins seems to be redundant, as any individual SR protein can commit a pre-mRNA for constitutive splicing, the role of the various SR proteins in alternative splicing of specific pre-mRNAs is distinct due in part to their ability to recognize and bind to unique consensus sequences (Bourgeois et al., 2004, Prog Nucleic Acid Res Mol Biol 78:37-88). Phosphorylation of the RS domain of SR proteins can lead to the regulation of their protein interactions, RNA binding, localization, trafficking, and role in alternative splicing (Caceres, et al., 1998, Genes Dev 12:55-66; Cao et al., 1997, RNA 3:1456-1467; Duncan et al., 1997, Mol Cell Biol 17:5996-6001; Misteli et al., 1998, J Cell Biol 143:297-307; Xiao et al., 1997, Genes Dev 11:334-344). Several cellular kinases that phosphorylate SR proteins have been identified, including SR protein Kinase (SRPKs) (Gui et al., 1994, Nature 369:678-682; Kuroyanagi et al., 1998, Biochem Biophys Res Commun 242:357-364), Cdc2-like kinases (Clks) (Ben-David et al., 1991, EMBO J. 10:317-325; Colwill et al., 1996, EMBO J 15:265-275), pre-mRNA processing mutant 4 (PRP4) (Kojima et al., 2001, J Biol Chem 276:32247-32256), and topoisomerase I (Rossi et al., 1996, Nature 381:80-82), Optimal phosphorylation of SR proteins is required for proper functioning as both hypo- and hyperphosphorylation of the RS domains is detrimental to their role in constitutive and alternative splicing (Prasad et al., 1999, Mol Cell Biol 19:6991-7000).

Besides its essential role in removing introns, splicing imprints the mRNA with a dynamic complex that is deposited around 20 nucleotides upstream of the exon-exon junction (Dostie et al., 2002, Curr Biol 12:1060-1067; Kataoka et al., 2004, J Biol Chem 279:7009-7013; Lau et al., 2003, Curr Biol 13:933-941; Tange et al., 2004, Curt Opin Cell Biol 16: 279-284). The exon junction complex (EJC) plays diverse roles in downstream mRNA biogenesis such as export to the cytoplasm, localization, non-sense mediated decay (NMD) and translation (Diem et al., 2007, Nat Struct Mol Biol 14:1173-1179; Hachet et al., 2004, Nature 428: 959-963; Le Hir et al., 2001, EMBO Rep 2:1119-1124; Le Hir et al., 2001, EMBO J. 20:4987-4997; Nott et al., 2004, Genes Dev 18:210-222; Wiegand et al., 2003, Proc Natl Acad Sci USA 100:11327-11332; Zhang d al., 2007, Proc Natl Acad Sci USA 104:11574-11579). Phosphorylation and possibly methylation of at least one component of the EJC, Y14, has been shown to regulate its interaction with other proteins involved in spliced mRNA biogenesis, but the signal that modulates these modifications has not been clearly identified (Hsu et al, 2005, J Biol Chem 280:34507-34512). On the other hand, the EJC-dependent phosphorylation of Upf1 has been shown to be critical for triggering NMD (Kashima et al., 2006, Genes Dev 20:355-367). Since upstream signaling seems to be essential for regulating components of the EJC and their function in spliced mRNA biogenesis, it is important to fully understand these signals and determine whether they modulate the expression of a subset of spliced mRNAs.

Aberrations in splicing due to mutations in the consensus sequences involved in exon-intron boundary recognition are responsible for up to 15% of inherited diseases (Krawezak et al., 1992, Hum Genet 90:41-54). In addition, defects in the splicing machinery itself due to the loss or gain of function of splicing factors and modulators are causes of a wide range of human ailments from cancer to neurodegenerative diseases (Garcia-Blanco et al., 2004, Nat Biotechnol 22:535-546; Licatalosi et al., 2006, Neuron 52:93-101; Venables, 2004, Cancer Res 64:7647-7654). Over the past few years, it has been established that both constitutive and alternative splicing are subject to regulation by upstream signaling pathways. This regulation is essential during development, in tissue specific expression of certain isoforms, during the cell cycle and in response to extrinsic signaling molecules (Hagiwara, 2005, Biochim Biophys Acta 1754:324-331; Schwerk et al., 2005, Mol Cell 19:1-13; Shin et al., 2004, Nat Rev Mol Cell Biol 5:727-738); however, the details of the underlying mechanisms or the specific proteins involved in such regulation remain largely unclear. The significant link between splicing defects and human diseases underscores the paramount importance for understanding the mechanisms of splicing, including the signaling pathways that regulate global splicing as well as splicing of specific subsets of transcripts.

Alternative splicing allows for a single gene to express different isoforms of mRNA, thus playing a major role in contributing to the cellular complexity in higher eukaryotes without the need to expand the genome (Blencowe, 2006, Cell 126:37-47). Global surveying of the human transcriptome estimates that up to 95% of multiexon genes undergo alternative splicing (Pan et al., 2008, Nat Genet 40:1413-1415; Wang et al., 2008, Nature 456:470-476). Importantly, these events are highly regulated by numerous splicing factors in a tissue type-, developmental stage-, and signal-dependent manner. Aberrations in splicing due to mutations in the pre-mRNA are responsible for up to 15% of inherited diseases (Krawczak et al., 1992, Hum Genet 90:41-54). In addition, defects in the splicing machinery itself, due to the loss/gain of function of splicing factors or their relative stoichiometry, are causes of a wide range of human ailments, ranging from cancer to neurodegenerative diseases (Cooper et al., 2009, Cell 136:777-793; Garcia-Blanco et al., 2004, Nat Biotechnol 22:535-546; Licatalosi et al., 2006, Neuron 52:93-101; Venables, 2004, Cancer Res 64:7647-7654). It has been established that splicing is subject to regulation by upstream signaling pathways. However, the details of the underlying mechanisms or the specific proteins involved in such regulation remain largely unclear. The significant link between splicing defects and human diseases underscores the paramount importance of understanding the mechanisms of splicing, including the signaling pathways that regulate general splicing as well as splicing of specific subsets of transcripts.

Small molecules have been essential in uncovering the mechanisms, regulations, and functions of many cellular processes, including DNA replication, transcription, and translation. While several recent reports have described screens for effectors of splicing, only a small number of constitutive or alternative splicing inhibitors have been identified (Kaida et al., 2007, Nat Chem Biol 3:576-583; Kotake et al., 2007, Nat Chem Biol 3:570-575; Levinson et al., 2006, RNA 12:925-930; Muraki et al., 2004, J Biol Chem 279:24246-24254; Pilch et al., 2001, Cancer Res 61:6876-6884; Soret et al., 2005, Proc Natl Acad Sci USA 102:8764-8769; Stoilov et al., 2008, Proc Natl Acad Sci USA 105:11218-11223; Sumanasekera et al., 2008, Biochem Sac Trans 36:483-490).

There is need in the art for a novel means to identify novel modulators of splicing or splicing dependent processes. The present invention fulfills this need.

SUMMARY OF THE INVENTION

The present invention includes a method of assessing the effect of a candidate general or alternative splicing inhibitor on RNA splicing. The method comprises the steps of: assessing the effect of a candidate general or alternative splicing inhibitor on expression, function, or activity of a first reporter construct expressed by a first recombinant cell, the first reporter construct comprising an open reading frame (ORF) interrupted by an intron comprising at least one stop codon; assessing the effect of the candidate general or alternative splicing inhibitor on expression, function, or activity of a second reporter construct expressed by a second recombinant cell, the second reporter construct comprising an intronless ORF; comparing the effect of the candidate general or alternative splicing inhibitor on expression, function, or activity of the first reporter construct with the effect of the candidate general or alternative splicing inhibitor on the expression, function, or activity of the second reporter construct; where when the candidate general or alternative splicing inhibitor significantly inhibits the expression, function or activity of the first reporter construct relative to the expression, function, or activity of the second reporter construct, then the candidate general or alternative splicing inhibitor is identified as an inhibitor of constitutive or alternative splicing.

In one aspect, the reporter construct encodes luciferase. In another aspect, the intronless reporter construct is Luc. In still another aspect, the intron-containing reporter construct is Luc I. In another aspect, the invention provides a general or alternative splicing inhibitor identified by the method of the invention. In still another aspect, the inhibitor inhibits cellular kinase activity. In yet another aspect, the inhibitor inhibits Cdc2-like kinases (Clks).

In another embodiment of the invention there is included a method of inhibiting general or alternative splicing of RNA in a cell. The method comprises contacting the cell with a general or alternative splicing inhibitor identified by the method of the invention.

In one aspect, the inhibitor inhibits cellular kinase activity. In another aspect, the inhibitor inhibits Cdc2-like kinases.

Still another embodiment of the invention provides a method of treating a subject afflicted with a disease or disorder caused by a defect in RNA splicing. The method comprises administering to a subject a therapeutically effective amount of a general or alternative splicing inhibitor identified according to the methods of the present invention, where the inhibitor contacts a cell affected by the defect in RNA splicing, where the inhibitor prevents the defect in RNA splicing in the cell, where the inhibitor alleviates the disease or disorder caused by the defect in RNA splicing.

In one aspect, the inhibitor is selected from the group consisting of clotrimazole, flunarizine, and chlorhexidine. In another aspect, the inhibitor inhibits cellular kinase activity. In still another aspect, the kinase is selected from the list consisting of SR protein kinase (SRPK), Cdc2-like kinases (Clks), pre-mRNA processing mutant 4 (PRP4) and topoisomerase I. In yet another aspect, the inhibitor inhibits Cdc2-like kinases (Clks). In another aspect, the subject is a mammal. In yet another aspect, the mammal is a human.

Still another embodiment of the invention provides for a kit for detecting general or alternative splicing inhibitors. The kit comprises a first recombinant cell expressing a first reporter construct, wherein the first report construct comprises an open reading frame (ORF); a second reporter construct expressed by a second recombinant cell, wherein the second reporter construct comprises an intronless ORF; wherein the effect of candidate general or alternative splicing inhibitors on expression, function or activity on the first reporter and second reporter is compared. In a further embodiment the first report construct encodes luciferase. In a still further embodiment the intronless reporter construct is Luc.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A through FIG. 1C, is a series of images depicting the characterization of a splicing reporter. FIG. 1A is a schematic diagram of the intron-containing (Luc I) and intronless (Luc) reporters. CP indicates the CL1 and PEST protein destabilizing sequences and ARE represents 5 tandem repeats of AUUUA sequence in the 3' UTR. FIG. 1B is a graph depicting the relative luciferase units detected for luciferase constructs transiently transfected into HeLa cells. There is more efficient expression of the Luc I as compared to Luc reporters. FIG. 1C is a graph depicting a marked decrease of luciferase expression upon inhibition of protein synthesis and transcription as a result of treatment with cycloheximide (CHX) or actinomycin B (ActD) for 4 hours.

FIG. 2, comprising FIG. 2A and FIG. 2B, is a series of images depicting a high-throughput screen for splicing modulators. FIG. 2A is a schematic diagram depicting the steps of the high-throughput screen. Cells stably expressing Luc I were treated with a library of >23,000 compounds for 4 hours and then screened for effectors of splicing (see Materials and Methods). Hits were counter-screened on Luc-expressing cells, and those compounds showing selective activity on Luc I were further studied as illustrated in the scheme. FIG. 2B is a scatter plot of a representative control plate of Luc I cells which shows a marked signal to noise ratio with a Z' value of 0.6 and CV=11%. Four columns on the plate were treated with ActD or CHX. The Control columns did not contain any cells and reflect the background/noise of the assay.

FIG. 4, comprising FIG. 4A through FIG. 4C, is a series of images depicting the distinct effects of splicing modulators on constitutive and alternative splicing of endogenous genes in cells. FIG. 4A is an image of a gel depicting the results of RT-PCR analysis of pre-mRNA splicing of an endogenous Coilin constitutive intron 2 as well as SR-dependent alternative splicing of exon 11 of the RON pre-mRNA upon treatment of cells with splicing modulators for 6 hours. FIG. 4B is a graph depicting the quantitative analysis of in vivo effects of splicing modulators, Real-time PCR analysis was carried on total RNA extracted from HeLa cells treated with clotrimazole, flunarizine, and chlorhexidine for 6 hours. For each endogenous gene a set of primers was designed to distinguish between exon-exon junction (spliced) and exon-intron junction (unspliced). The Coilin and ILF introns analyzed are U2-dependent, whereas CCDC56 and 1K are U12-dependent. Three independent replicates were used for each treatment and DMSO values were set to 1. FIG. 4C depicts real time qPCR analysis of introns from various endogenous genes. Each bar represents the average of results from three measurements, and data are presented relative to the level for DMSO, which was set to 1. All qPCR measurements were normalized to the level for β-actin.

FIG. 5, comprising FIG. 5A is an image of a gel depicting analysis of constitutive splicing of the CδC pre-mRNA in the presence of clotrimazole, flunarizine, and chlorhexidine for 90 minutes. None of the compounds impairs constitutive splicing in vitro. Splicing intermediates are depicted to the left of the gel, and molecular size markers are indicated to the right of the gel. Fully spliced mRNA is indicated with an arrow and corresponds to 140 nucleotides. FIG. 5B is images of gels depicting SR protein-dependent splicing of Tat exon2-3, HβΔ6 and μC3-C4 pre-mRNA analyzed in the presence of 50 and 100 μM of chlorhexidine that resulted in dose-dependent enhancement of splicing. Splicing intermediates are depicted to the left of the gels, and molecular size markers are indicated to the right of the gels. Arrows point to the altered levels of the spliced mRNA, which are 371, 367, and 271 nucleotides for Tat2-3, HβΔ6, and μC3-C4, respectively.

FIG. 6, comprising FIG. 6A, left panel, depicts a gel of total protein extracts from cells treated with 0, 2, 5, 5, 10, 15, and 20 μM chlorhexidine for 6 hours, separated on polyacrylamide gels and phospho-SR proteins detected using the 1H4 monoclonal antibody. FIG. 6A, right panel, is a histogram representing the quantification of the band intensities using LiCor software. FIG. 6A, left, depicts a gel depicting total levels of both SR proteins as well as other proteins involved in mRNA biogenesis were analyzed in protein extracts from cells treated with 0, 2.5, 5, 10, 15, and 20 μM chlorhexidine for 6 hours. Antibodies used in this blot do not distinguish between phosphorylated and unphosphorylated isoforms. FIG. 6B, right panel, depicts a histogram representing the quantification of the band intensities using LiCor software. FIG. 6A depicts total protein extracts from cells treated with 0, 10, and 20 μM chlorhexidine or TG003 for 6 h, separated by SDS-PAGE, and phosphorylated SR proteins were detected by Western blotting using the SR protein phospho-specific monoclonal antibody (1H4). Quantification of the phosphorylated SR proteins is depicted in the histogram. Values are presented relative to the level for DMSO, which was set to 1 (dashed line). FIG. 6B is a graph depicting in vitro kinase profiling of chlorhexidine. The ability of recombinant kinases known to target SR proteins to phosphorylate an SR-rich substrate in vitro in the presence of either DMSO or increasing concentrations of chlorhexidine was tested in vitro. Activity in the presence of DMSO was set to 100%.

FIG. 9, comprising FIGS. 9A through 9C, depicts confirmation data of the exon array. FIG. 9A, a graph, shows real-time PCR for a select number of exons identified by the exon array. FIG. 9B, a series of gels, illustrates RT-PCR confirmation of alternative splicing events identified by the exon array. FIG. 9C, a series of gels, depicts cell type specificity of chlorhexidine on NOS1AP and OUT.

FIG. 10, comprising FIG. 10A is a Venn diagram of the affected transcripts from the exon arrays. FIG. 10B is a graph depicting the breakdown of the splicing modulators-mediated alternative splicing events identified by exon arrays.

FIG. 11 is a two part table that depicts a listing of 10 hits from the splicing screen that exhibit differential effect on Luc-I vs. Luc cells.

DETAILED DESCRIPTION OF THE INVENTION

Figure 3:
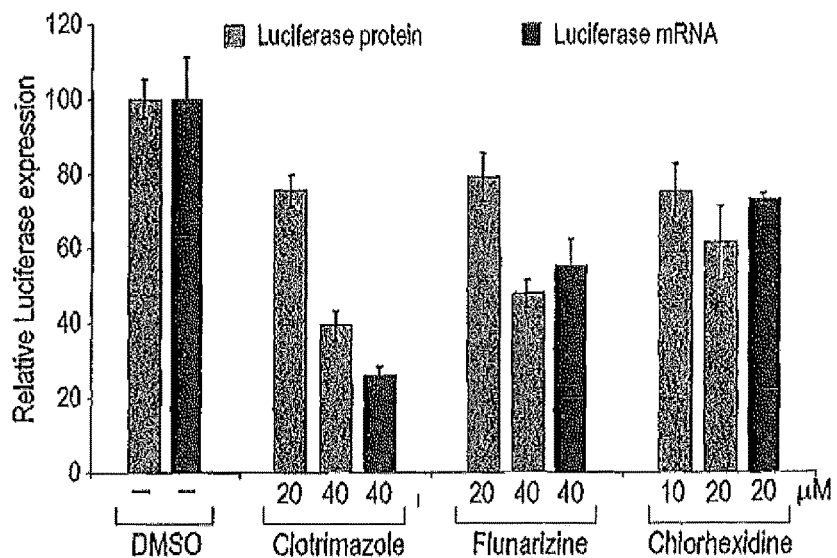
FIG. 3 is a graph depicting the effect of splicing inhibitors on luciferase protein and mRNA expression. Luc I cells treated with varying concentrations of compounds for 4 hours show a significant reduction of luciferase signal (blue bars) as well as luciferase spliced mRNA (red bars). Data are presented as percentages of the level for DMSO-treated cells, and error bars denote the standard deviations for three independent experiments.
Figure 3:
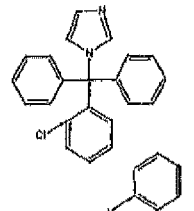
Figure 3:
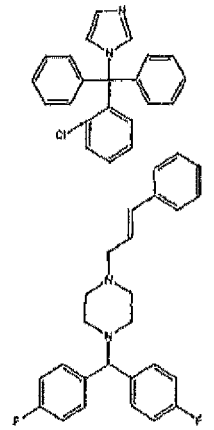
Figure 3:
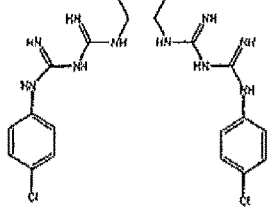

The present invention is based on the discovery of a cell-based system to identify novel modulators of splicing or splicing dependent processes. The cell-based system of the present invention utilizes a fast and highly sensitive reporter, preferably luciferase, that responds to defects in the splicing machinery itself and is sensitive to changes in the signals that regulate splicing dependent processes such as those that modulate the DC, splicing-dependent export, localization or translation efficiency.

The present invention further uses the cell-based screen to identify several small molecules that modulate both constitutive and alternative splicing. Accordingly, the present invention includes general or alternative splicing inhibitors identified using the assay described herein.

The present invention also provides both prophylactic and therapeutic methods of treating a subject at risk of, susceptible to, or having a disease, disorder, or condition associated with aberrant or unwanted target RNA expression or activity using general or alternative splicing inhibitors of the present invention. In one embodiment, a target RNA of the invention is any aberrantly spliced or unwanted pre-mRNA that results in, causes, produces, or pre-disposes a subject to a disease or disorder. In another embodiment, the invention provides a method for preventing in a subject, a disease, disorder, or condition associated with aberrant or unwanted RNA expression or activity, the method comprising administering to the subject a therapeutic agent comprising a general or alternative splicing inhibitor of the invention. The present invention further provides methods of treating a subject afflicted with a disease or disorder characterized by aberrant or unwanted expression or activity of a target RNA molecule.

The present invention further details a kit that may be directed to specifically detecting a general or alternative splicing inhibitor of the invention. In another embodiment, a kit of the invention may also comprise a general or alternative splicing inhibitor of the invention as well as an applicator for administering the inhibitor to a subject in need thereof.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Antisense" refers particularly to the nucleic acid sequence of the non-coding strand of a double stranded DNA molecule encoding a protein, or to a sequence that is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease, or disorder, the frequency with which such a symptom is experienced by a patient, or both, are reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, gene expression and translation of the coding sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

An "inducible" promoter is a nucleotide sequence which, when operably linked with a polynucleotide which encodes or specifies a gene product, causes the gene product to be produced substantially only when an inducer which corresponds to the promoter is present.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "recombinant DNA" as used herein is defined as DNA produced by joining pieces of DNA from different sources.

The term "recombinant polypeptide" as used herein is defined as a polypeptide produced by using recombinant DNA methods.

The term "recombinant cell" as used herein is defined as a cell expressing either recombinant DNA or a recombinant polypeptide.

By the term "specifically binds," as used herein, is meant a molecule, such as an antibody, which recognizes and binds to another molecule or feature, but does not substantially recognize or bind other molecules or features in a sample.

As used herein, the terms "candidate compound" and "candidate general or alternative splicing inhibitor" refer to a composition being evaluated for the ability to modulate pre-mRNA splicing, Candidate compounds can be natural or synthetic compounds, including, for example, small molecules, compounds contained in extracts of animal, plant, bacterial or fungal cells, as well as conditioned medium from such cells.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

The term "treatment," as used herein, refers to reversing, alleviating, delaying the onset of, inhibiting the progress of, and/or preventing a disease or disorder, or one or more symptoms thereof, to which the term is applied in a subject. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

It is understood that any and all whole or partial integers between any ranges set forth herein are included herein.

DESCRIPTION

The present invention includes a cell-based reporter system with advantageous properties that can be used for the systematic discovery of modulators of splicing and splicing dependent properties. A further description of the invention is contained herein.

Cell-Based High Throuhput Screening Method for Detecting General or Alternative Splicing Inhibitors The present invention provides a method of identifying general or alternative splicing inhibitors using a real-time cell-based selection system. The method employs at least one recombinant cell expressing a reporter construct. Preferably, the cell is stably transfected with the reporter construct. Methods of transfecting a cell with a reporter construct, as well as producing stably transfected cell lines expressing a reporter construct, are well known in the art.

One embodiment of the present invention provides a method of assessing the effect of a candidate general or alternative splicing inhibitor on pre-mRNA splicing. The method comprises the steps of (a) assessing the effect of a candidate general or alternative splicing inhibitor on expression, function, or activity of a first reporter construct expressed by a first recombinant cell, where the first reporter construct comprises an open reading frame (ORF) interrupted by an intron comprising at least one stop codon; (b) assessing the effect of the candidate general or alternative splicing inhibitor on expression, function, or activity of a second reporter construct expressed by a second recombinant cell, where the second reporter construct comprises an intronless ORF; and (c) comparing the effect of the candidate general or alternative splicing inhibitor on expression, function, or activity of the first reporter construct with the effect of the candidate alternative splicing inhibitor on the expression, function, or activity of the second reporter construct, wherein when the candidate general or alternative splicing inhibitor significantly inhibits the expression, function or activity of the first reporter construct relative to the expression, function, or activity of the second reporter construct, then the candidate general or alternative splicing inhibitor is identified as an inhibitor of constitutive or alternative splicing.

The reporter construct can be cloned into any number of different vectors. However, the present invention should not be construed to be limited to any particular vector. Instead, the present invention should be construed to encompass a wide plethora of vectors which are readily available and/or well-known in the art. For example, a reporter construct of the invention can be cloned into a vector such as, but not limited to, a plasmid, a phagemid, a phage derivative, an animal virus, and a cosmid. Vectors of particular interest include expression vectors, replication vectors, probe generation vectors and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

The reporter construct generally includes a promoter, a coding sequence and a polyadenylation signal. A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The coding sequence can include a reporter sequence selected from the group consisting of an enzyme (e.g., luciferase, alkaline phosphatase, beta-galactosidase, chloramphenicol acetyltransferase (CAT), secreted alkaline phosphatase, etc.), a bioluminescence marker (e.g., green fluorescent protein (GFP, U.S. Pat. No. 5,491,084), etc.), a surface-expressed molecule (e.g., CD25), a secreted molecule (e.g., IL-8, IL-12 p40, TNF-α, etc.), and other detectable protein products known to those of skill in the art. Preferably, the coding sequence encodes a protein having a level or an activity that is quantifiable.

In one aspect of the invention, the reporter construct of the present invention is designed such that the open reading frame (ORF) is intronless. Expression of the intronless reporter construct in a recombinant cell yields a full length, functional reporter protein and is not affected by general or alternative splicing inhibitors.

In another aspect of the invention, the ORF of the reporter construct is interrupted by an intron comprising at least one stop codon. In the absence of a general or alternative splicing inhibitor, an intron present in the ORF of a reporter construct will be spliced out and a full-length functional reporter protein is expressed by the cell. In the presence of a general or alternative splicing inhibitor, the intron within the ORF of the reporter construct is not spliced out and the resulting reporter protein is truncated and has reduced expression and/or functionality.

A reporter construct of the invention may further comprise destabilizing sequences to shorten the half-life of both the resulting reporter mRNA and reporter protein and thereby decrease the response time of the reporter gene to candidate alternative splice inhibitors. Examples of such destabilizing sequences include, but are not limited to, CL1 and PEST added to the C-terminus of the protein or 5 consecutive AUUU elements added to the 3' UTR.

The method of identifying general or alternative splicing inhibitors according to the present invention comprises a two step assay. In the first step of the assay, a recombinant cell expressing a reporter construct wherein the ORF of the coding sequence comprises an intron with at least one stop codon is contacted with a candidate general or alternative splicing inhibitor and the expression, activity, or function of the reporter protein is measured relative to a control. A control of the present invention comprises the vehicle used to prepare the candidate compound or other solution or agent that does not contain the candidate compound and is not expected to affect alternative splicing. If the candidate alternative splice inhibitor significantly inhibits the expression, activity, or function of the reporter protein relative to control, the candidate inhibitor is further screened using a recombinant cell expressing an intronless reporter construct. A significant inhibition of reporter protein expression, function or activity is an inhibition more than one times, two times, three times, four times, or five times the standard deviation of reporter construct expression, function or activity when compared to control treated cells.

In the second step of the assay, a recombinant cell expressing an intronless reporter construct is contacted with the same candidate general or alternative splicing inhibitor and the expression, activity, or function of the reporter protein is measured. If the candidate alternative splicing inhibitor has a significantly different effect on the expression, function, or activity of the intronless reporter construct as compared to the intron containing reporter construct, then said candidate compound is identified as an inhibitor of constitutive or alternative splicing.

In a preferred embodiment of the invention, the reporter construct comprises a sequence encoding luciferase. In one aspect, the ORF of the reporter construct comprises an intron with multiple stop codons, referred to herein as Luc1, whereby, if the intron is not spliced out of the coding region, produces a truncated luciferase protein with limited functionality. In another aspect, the ORF of the reporter construct, referred to herein as Luc, is intronless. In the presence of an alternative splice inhibitor, the recombinant cell expressing the Luc1 reporter construct produces a non-functional luciferase protein but has no effect of the full length luciferase protein produced by the Luc reporter construct.

It will be readily appreciated by a skilled artisan that the resulting reporter construct may be detected at the protein or nucleic acid level using any method known in the art. Such methods are well known in the art and include but are not limited to Western blots, Northern blots, Southern blots, ELISA, immunoprecipitation, immunofluorescence, flow cytometry, immunocytochemistry, nucleic acid hybridization techniques, nucleic acid reverse transcription methods, and nucleic acid amplification methods. In some embodiments of the invention immunohistochemistry techniques are provided that utilize antibodies to detect a reporter protein, such as Western blot or ELISA. A reporter construct may also be detected by nucleic acid techniques, including, but not limited to, hybridization techniques and RT-PCR. The invention should not be limited to any one method of protein or nucleic acid detection method recited herein, but rather should encompass all known or heretofor unknown methods of detection as are, or become, known in the art.

In another aspect of the invention, the reporter construct may be detected or quantified using a functional assay to detect and/or quantify the activity of the reporter protein. Examples of such assays include enzyme assays, bioluminescence assays, luciferase activity assays, and the like, and are well known in the art. Depending on the assay, quantitation of the amount of gene expression allows one to determine whether there is a difference in reporter protein expression or functionality between cells expressing a coding sequence comprising an intron or cells expressing an intronless reporter construct. Quantitation of gene expression in a cell may show similar amounts of modulation at the level of accumulation of target mRNA or translation of target protein. As an example, the efficiency of modulation may be determined by assessing the amount of gene product in the cell; pre-mRNA or mRNA may be detected with a hybridization probe having a nucleotide sequence outside the region used for the oligonucleotide reagent, or translated polypeptide may be detected with an antibody raised against the polypeptide sequence of that region.

In order to screen multiple candidate compounds simultaneously, recombinant cells expressing a reporter construct of the invention may be seeded onto multi-well plates using an automated cell dispenser and allowed to grow in an incubator. Candidate compounds and controls may be applied to multiple wells simultaneously at one or more dosage concentrations prior to measuring and comparing reporter construct expression, function or activity.

General or Alternative Splicing Inhibitors

The present invention encompasses a class of synthetic compounds known as constitutive or alternative splicing inhibitors that are identified according to the methods of the present invention. In one embodiment of the present invention, a general or alternative splicing inhibitor of the present invention is any molecule, compound, or agent that is able to affect alternative pre-mRNA splicing, splicing machinery, or splicing dependent processes in a cell. In another embodiment of the invention, a general or alternative splicing inhibitor is any molecule, compound, or agent that affects the activity of various cellular kinases including SR protein kinase (SRPK), Cdc2-like kinases (Clks), pre-mRNA processing mutant 4 (PRP4) and topoisomerase I. In a preferred embodiment of the invention, a general or alternative splicing inhibitor is a small molecule.

When the general or alternative splicing inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making said libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery versus biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In one embodiment of the invention, a small molecule general or alternative splicing inhibitor of the invention is selected from a panel of FDA-approved drugs and inhibitors of various cell functions. In another embodiment, a small molecule alternative splicing inhibitor of the invention is a specific inhibitor of the CLK family of SR protein kinases. In one embodiment of the invention, a small molecule general or alternative splicing inhibitor of the invention comprises clotrimazole, flunarizine, or chlorhexidine.

Method of Treating Aberrant Pre-mRNA Splicing

The present invention provides methods for both prophylactic and therapeutic treatment of a subject at risk of, susceptible to, or having a disease, disorder, or condition associated with aberrant or unwanted pre-mRNA splicing using a general or alternative splicing inhibitor identified according to the methods described herein. In one embodiment, a subject is an animal. In another embodiment, a subject is a mammal. In another aspect, a subject is a human. The method comprises administering to a subject a therapeutic agent comprising a general or alternative splicing inhibitor identified according to the methods of the present invention. In one embodiment, the general or alternative splicing inhibitor is a small molecule. In another embodiment, the general or alternative splicing inhibitor is selected from the list consisting of clotrimazole, flunarizine, chlorhexidine, or any combination thereof.

Subjects at risk for a disease caused by or contributed to by aberrant or unwanted pre-mRNA splicing can be administered a prophylactic agent comprising a general or alternative splicing inhibitor identified according to the methods of the present invention. In one embodiment, the general or alternative splicing inhibitor is a small molecule. In another embodiment, the general or alternative splicing inhibitor is selected from the list consisting of clotrimazole, flunarizine, chlorhexidine, or any combination thereof.

It will be appreciated by the skilled artisan that a general or alternative splicing inhibitor useful in the prophylactic or therapeutic treatment of a subject at risk of, susceptible to, or having a disease, disorder, or condition associated with aberrant or unwanted pre-mRNA splicing should not be considered to be limited to those inhibitors recited herein, but rather should be considered to include any general or alternative splicing inhibitor identified according to the methods of the assay described herein.

A general or alternative splicing inhibitor may be administered to a subject in need thereof at a dose of 0.1, 0.5, 1, 5, 10, 15, 20, 25, 30, 35, 40, 45, 50, 55, 60, 65, 70, 75, 80, 85, 90, 95, or 100 µM or any whole or partial integer included between any range thereof.

Pharmaceutical Compositions and Therapies

A general or alternative splicing inhibitor of the invention may be administered to a subject in a pharmaceutical composition. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below.

Depending on the particular target RNA and the dose of general or alternative splicing inhibitor delivered, this process may modulate function of the target gene. The consequences of modulation of the target RNA can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats and dogs.

Pharmaceutical compositions that are useful in the methods of the invention may be prepared, packaged or sold in formulations suitable for ophthalmic, oral, parenteral, intranasal, buccal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier and any additional ingredients in a pharmaceutical composition of the invention will vary, depending upon the identity, size and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound and the like. In particular, parenteral administration is contemplated to include, but is not limited to, intraocular, intravitreal, subcutaneous, intraperitoneal, intramuscular, intrasternal injection, intratumoral and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes and implantable sustained-release or biodegradable formulations. Such formulations may further comprise one or more additional ingredients including, but not limited to, suspending, stabilizing or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution and fixed oils such as synthetic mono- or di-glycerides. Other parentally-administrable formulations which are useful include those which comprise the active ingredient in microcrystalline form, in a liposomal preparation or as a component of a biodegradable polymer system. Compositions for sustained release or implantation may comprise pharmaceutically acceptable polymeric or hydrophobic materials such as an emulsion, an ion exchange resin, a sparingly soluble polymer or a sparingly soluble salt.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The therapeutic and prophylactic methods of the invention thus encompass the use of pharmaceutical compositions comprising a splice altering oligonucleotide of the invention to practice the methods of the invention. The precise dosage administered will vary depending upon any number of factors, including but not limited to, the type of animal and type of disease state being treated, the age of the animal and the route of administration.

The compound may be administered to a subject as frequently as several times daily, or it may be administered less frequently, such as once a day, once a week, once every two weeks, once a month or even less frequently, such as once every several months or even once a year or less. The frequency of the dose will be readily apparent to the skilled artisan and will depend upon any number of factors, such as, but not limited to, the type and severity of the disease being treated, the type and age of the subject, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Kits

Kits for practicing the methods of the invention are further provided. By "kit" is intended any manufacture (e.g., a package or a container) comprising at least one reagent, e.g., a recombinant cell, an antibody, a nucleic acid probe, etc. In one embodiment, a kit may be directed to specifically detecting a general or alternative splicing inhibitor of the invention. In another embodiment, a kit of the invention may also comprise a general or alternative splicing inhibitor of the invention as well as an applicator for administering the inhibitor to a subject in need thereof. The kit may be promoted, distributed, or sold as a unit for performing the methods of the present invention. Additionally, the kits may contain a package insert describing the kit and including instructional material for its use.

Positive and/or negative controls may be included in the kits to validate the activity and correct usage of reagents employed in accordance with the invention. Controls may include samples, such as tissue sections, cells fixed on glass slides, etc., known to be either positive or negative for the presence of the biomarker of interest. The design and use of controls is standard and well within the routine capabilities of those of ordinary skill in the art.

One of skill in the art will further appreciate that any or all steps in the methods of the invention could be implemented by personnel or, alternatively, performed in an automated fashion.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Reporter Construction and Generation of Stable Cell Lines

The intron containing luciferase reporter was generated by inserting a 132 nucleotide chimeric β-globin intron at position 1344 of firefly luciferase gene. The luciferase protein is destabilized as described by the manufacturer (Promega) using both a PEST protein degradation sequence as well as a CL1 sequence. In order to destabilize the mRNA, five AUUUA repeats were introduced into the 3'UTR of the reporter luciferase gene. Both intron-containing and intronless luciferase were transcribed from a CMV promoter.

To generate stable cell lines, the reporter constructs were transfected into Hela and/or HEK293T cells using EFFECT- ENE® (Qiagen) for 24 hours, followed by selection with hygromycin for 2-3 weeks. Single cell clones were then tested for expression of luciferase. The dual luciferase assay was performed according to manufacturer recommendation (Promega). The integrity of the inserted reporter as well as the maintenance of the intronic sequence was tested by PCR of the genomic DNA.

Chemical Compounds and HTS

A library of >23,000 small molecule inhibitors of diverse chemistry, including known bioactive compounds and FDA-approved drugs, was assembled from several commercial sources (Microsource Diversity, Sigma-Aldrich, BioMol, Tocris, Lopac, Prestwick, Maybridge, and Chembridge) and maintained at 2 mM stock concentration in DMSO. For confirmation studies, clotrimazole, flunarizine, and chlorhexidine were purchased from Sigma-Aldrich.

For HTS, 2000 cells per well were seeded on white-1,536 well plates using an automated cell dispenser and allowed to grow overnight. Cells were treated with compounds in duplicate wells at a final concentration of 20 µM using Beckman robotics. The first and last two columns of each plate were treated with DMSO and used as internal controls and assigned an activity of 100%. Compounds were administered to the central wells in duplicates. Briefly, 70 nl of compounds diluted in growth medium (final concentration of 20 µM) was added to wells by using a Pintool (V&P Scientific) attached to a BIOMEK® FX workstation (Beckman Coulter), and the plates were incubated for an additional 4 h. Cells were washed once with PBS. Cell lysis and addition of luciferase substrate were combined into one step using ONE-GLO™ reagent (Promega) and luminescence signals were measured by an ENVISION® Reader (Perkin Elmer) with standard luminescence settings. For each plate the activity from DMSO treated wells was normalized to 100% and the percentage activity from each well was calculated. Compounds that caused a change in luciferase signal more than 2× standard deviation were evaluated in the same manner as above but using intronless luciferase expressing cells. "Hits" were defined as those compounds that showed a significantly different effect on intron-containing compared to intronless luciferase. Dose responses of these select hits were performed in plates using concentrations ranging from 1 to 100 µM.

RNA Extraction and Reverse Transcription PCR (RT-PCR)

To analyze the effect of the splicing inhibitors on reporter RNA and endogenous RNA splicing, HeLa cells were seeded in 12-well plates for 24 hours, followed by treatment with the various compounds for the indicated time. Total RNA was extracted using RNAeasy kit (Qiagen) according to manufacturer instructions, followed by cDNA synthesis from 1 µg total RNA using the RT-for-PCR reagent (Clontech). Nonquantitative PCR was performed using 5 µl of diluted cDNA and Pfx DNA polymerase (Invitrogen). Quantitative real-time PCR using 5 µl of the same cDNA and relative quantification analysis were performed with an Applied Biosystems 7500 fast system by using SYBR green dye chemistry in accordance with the manufacturer's recommendations. All primers are listed in Table 1 below.

TABLE 1

Primers used for RT-PCR

| | | |
|---|---|---|
| Coilin exon2F | GCTCAAATGGTGGTGGACAGG | SEQ ID NO: 1 |
| Coilin exon3R | GCAGCTGCTAACAGTGGTAACAGAC | SEQ ID NO: 2 |
| RON exon10F | TGTGAGAGGCAGCTTCC | SEQ ID NO: 3 |
| RON exon12R | TAGCTGCTTCCTCCGCC | SEQ ID NO: 4 |
| Casp9 exon2F | GCTCTTCCTTTGTTCATCTCC | SEQ ID NO: 5 |
| Casp9 exon7R | CATCTGGCTCGGGGTTACTGC | SEQ ID NO: 6 |
| Coilin unsplicedF | TGTGTGGAGTTCATGTCATGGA | SEQ ID NO: 7 |
| Coilin unsplicedR | TGGGTGTCTCTACTGGATTCTGAAA | SEQ ID NO: 8 |
| CCDC56 exon1-2 unsplicedF | CCTGGTGTTGGCTATTTGTATCC | SEQ ID NO: 9 |
| CCDC56 exon1-2 unsplicedR | GCCCTCTTGCACACTCTGTTC | SEQ ID NO: 10 |
| ILF2 exon4-5 unsplicedF | AGGCCTTGCTGAAGAGGAATC | SEQ ID NO: 11 |
| ILF2 exon4-5 unsplicedR | GACATTTCTGGAAGACAGCCAAA | SEQ ID NO: 12 |
| ILF2 exon5-6 unsplicedF | GATTGTGGCTCCAGGGACAT | SEQ ID NO: 13 |
| ILF2 ex5-6 unsplicedR | AAGCTGCCCTTTCCTAAAACTAAAT | SEQ ID NO: 14 |
| IK exon14-15 unsplicedF | GGGAAGGCACAGAATCATATCC | SEQ ID NO: 15 |
| IK exon14-15 unsplicedR | AAATTCAGCGTAAAAGGGAAGGA | SEQ ID NO: 16 |
| DIAPH1 int11 F | CCCTGATCCCTGTGTGGAAT | SEQ ID NO: 17 |
| DIAPH1 int11 R | GACACATAAGCCTGATGCTCTGTT | SEQ ID NO: 18 |
| CK1A1 int1 F | CGAACCTCGTCCGCTGTCT | SEQ ID NO: 19 |
| CK1A1 int1 R | GTTCCCCCAACCTTTCTATCG | SEQ ID NO: 20 |

TABLE 1-continued

Primers used for RT-PCR

| | | |
|---|---|---|
| EIF3D int1 F | GAGACTCGTTGTCTTGGTATTATGATGT | SEQ ID NO: 21 |
| EIF3D int1 R | GCAGCAGCCCGCAAAG | SEQ ID NO: 22 |
| ERBB2IP int16 F | TTATTTGCCCCTTATACAAACTTAGCT | SEQ ID NO: 23 |
| ERBB2IP int16 R | TGTCTCACATACCAAGAGCCATATTT | SEQ ID NO: 24 |
| ETF1 int10 F | GCTTCCGGTGAGGTGCTTATT | SEQ ID NO: 25 |
| ETF1 int10 R | TGCACCTGCTGCGTCAA | SEQ ID NO: 26 |
| ETF1 int2 F | CGCATGGCCGGATGAG | SEQ ID NO: 27 |
| ETF1 int2 R | AGATCCAGAAGGCGGGAGTT | SEQ ID NO: 28 |
| FGF18 int1 F | CTGACTCTTCGACTGCGTGTCT | SEQ ID NO: 29 |
| FGF18 int1 R | GTAAACACCTGCGGGAAACAG | SEQ ID NO: 30 |
| Gemin3 int1 F | GGCGTGTTCTCATACGTTTTG | SEQ ID NO: 31 |
| Gemin3 int1 R | GGGTCTCCTGAGATTCCCCTAGT | SEQ ID NO: 32 |
| hnRNP M int7 F | CGTGGAATAGGCACTGTTACTTTTG | SEQ ID NO: 33 |
| hnRNP M int7 R | ATTCCTGCAGAAGGATACATATAGCTT | SEQ ID NO: 34 |
| hnRNP M int8 F | CACGTCAAGATGGTAAGTCAGTAGGA | SEQ ID NO: 35 |
| hnRNP M int8 R | AACATACTGCACCCTATTTAACTTAGAC | SEQ ID NO: 36 |
| MTRR int1 F | TCGAGCCGATCATCTGATTTC | SEQ ID NO: 37 |
| MTRR int1 R | TCAAATTAAGGAGAGTGTACGAATGAA | SEQ ID NO: 38 |
| NR3C1 int1 F | CAGTGAGCGGCAGGATGAA | SEQ ID NO: 39 |
| NR3C1 int1 R | TGCACAGCTGAGGGCAAA | SEQ ID NO: 40 |
| NR3C1 int2 F | TGCTAAAGCAATGCAGTGAACA | SEQ ID NO: 41 |
| NR3C1 int2 R | GCAAGAACCCTGTGAGCAAGA | SEQ ID NO: 42 |
| NOP2 int16 F | TGGTCAGCCAGATGGTCTGA | SEQ ID NO: 43 |
| NOP2 int16 R | AGGGTCAAGTGGCTGGTAGGT | SEQ ID NO: 44 |
| POM121 int2 F | TCTGAATGCTCTCAGTTGAATGG | SEQ ID NO: 45 |
| POM121 int2 R | TGCCCACAAGGAATTAAATGG | SEQ ID NO: 46 |
| PSMB2 int4 F | TTTCCTCCCCTTGCCTAAGTG | SEQ ID NO: 47 |
| PSMB2 int4 R | AGCACAAAAGCATCCCTGTGT | SEQ ID NO: 48 |
| RPL23 int1 F | GACTGGATTAGGCCCTGGTTT | SEQ ID NO: 49 |
| RPL23 int1 R | GCAATTACTCCTGCAAGGCATA | SEQ ID NO: 50 |
| ZNF622 int1 F | AAATGATGAGGGAAGGTGGTTTAG | SEQ ID NO: 51 |
| ZNF622 int1 R | CCAAACCTGCTGGCCAGAT | SEQ ID NO: 52 |
| SRRM2 int8 F | CCACCTTAGTGGGAGGGAGTT | SEQ ID NO: 53 |
| SRRM2 int8 R | CTCACGTATCCCTCAACCCTTT | SEQ ID NO: 54 |
| SRRM2 int9 F | TGCACAGACCATTCGGAAGA | SEQ ID NO: 55 |
| SRRM2 int9 R | TGCTTTAGCCTGTCAGCTCCTA | SEQ ID NO: 56 |
| BRWD2 int15 F | CCGCCAGACCGTAGTCTCA | SEQ ID NO: 57 |
| BRWD2 int15 R | AGACATGATGCTAATGGCACAAA | SEQ ID NO: 58 |
| DOCK5 int41 F | AATGCGGAGAAGATGACCAGTAC | SEQ ID NO: 59 |

TABLE 1-continued

Primers used for RT-PCR

| | | |
|---|---|---|
| DOCK5 int41 R | CCCGGAAAGGATACACTGCTT | SEQ ID NO: 60 |
| TMEM1 int12 F | CCTCTCCGCTCCAGCTACCT | SEQ ID NO: 61 |
| TMEM1 int12 R | TGCTTGCGCTCCTCTTCAGT | SEQ ID NO: 62 |
| TMEM1 int16 F | CCGAAGCCATGCTCATCCT | SEQ ID NO: 63 |
| TMEM1 int16 R | CACCTCACCTCTCGTGTTGGA | SEQ ID NO: 64 |
| Caspase9 int3 F | GGAGAGCCCGGGTTTACG | SEQ ID NO: 65 |
| Caspase9 int3 R | GCAGAAGTTCACATTGTTGATAATGA | SEQ ID NO: 66 |
| RON int10 F | CACCCAGTGCCAACCTAGTTC | SEQ ID NO: 67 |
| RON int10 R | CCCTATCCCTTACACTTACCTCAAAC | SEQ ID NO: 68 |
| SMN int3 F | CGAGATGATAGTTTGCCCTCTTC | SEQ ID NO: 69 |
| SMN int3 R | TCCCCAACTTTCCACTACAAAAG | SEQ ID NO: 70 |
| DNAJB2 int9 F | GAGCGGGTGGAAGTGGAGGAGGAT | SEQ ID NO: 71 |
| DNAJB2 int9 R | TCAGAGGATGAGGCAGCGAGAGGC | SEQ ID NO: 72 |
| TRA2Beta int1 F | GGTAGAGTTAGAGCCCGTGCGGAG | SEQ ID NO: 73 |
| TRA2Beta int1 R | GGCCTCCCTCCTTCACGACCAAAG | SEQ ID NO: 74 |

In Vitro Splicing

The pre-mRNA minigenes CδC14-15 (chicken delta chrystaline), HIV Tat 2-3, and HβΔ6 (globin 1-2) and their splicing conditions were previously described (Kataoka et al., 2004, J Biol Chem 279:7009-7013; Mayeda et al., 1999, Mol Cell Biol 19:1853-1863). Briefly, the pre-mRNAs were labeled with $^{32}$P-UTP by in vitro transcription with SP6 polymerase followed by gel purification. Splicing reactions were performed using HEK 293T total (CDC14-15) or HeLa nuclear (Tat2-3, µC3-C4, and HβΔ6) extract in the presence of DMSO or the specified compounds were incubated for 90 to 120 minutes at 30° C. Splicing products were purified by TRIZOL® for CβC14-15 or by proteinase K digestion followed by phenol-chloroform extraction for HIV Tat 2-3, µC3-C4 and H βΔ6, and resolved via denaturing polyacrylamide gel electrophoresis (PAGE).

Quantitative Western Blot Analysis

Protein samples were resolved by SDS-PAGE and transferred to a 0.2-µm nitrocellulose membrane, Membranes were blocked in Li—COR blocking buffer at 4° C. with gentle rocking overnight. Primary antibodies were diluted in Li—COR blocking buffer+0.2% TWEEN®-20 and incubated with the membranes for 2 hour at room temperature (RT). The membranes were washed 4 times, 15 minutes with PBS containing 0.1% TWEEN®-20. Secondary antibodies (IR dye 800, Rockland) were diluted 1/5000 in Li—COR blocking buffer+0.2% TWEEN®-20 and incubated with the membranes for 1 hr. The membranes were washed 4 times, 15 minutes with PBS containing 0.1% TWEEN®-20. The membranes were then rinsed with PBS and detection of the infrared-conjugated antibodies was done using an ODYSSEY® infrared imaging system. Anti phospho-SR proteins (1H4), SF2/ASF, SRm160, and SRp20 antibodies were purchased from Abcam, Anti eiF4A3 (3F1) and Magoh (18G12) were previously described (Chan et al., 2004, RNA 10:200-209; Kataoka et al., 2000, Mal Cell 6:673-682).

In Vitro Kinase Profiling

Several activated recombinant kinases including Clk1-4, SRPK1-2, JNK and ERK were incubated with a synthetic SR-rich substrate peptide in the present of 50 µM ATP and $^{32}$P-ATP cocktail and kinase assay buffer (5 mM MOPS, pH 7.2, 2.5 mM β-glycerol-phosphate, 5 mM MgCl$_2$, 1 mM EGTA, 0.4 mM EDTA, 0.05 mM DTT) for 20 minutes. Either DMSO or chlorhexidine was also added at various concentrations. The assay was terminated by spotting 10 µl of the reaction mixture onto phosphocellulose P81 plate, which was washed 3 times for 15 minutes each in a 1% phosphoric acid solution. The radioactivity on the P81 plate was counted in the presence of scintillation fluid in a TriLux scintillation counter.

Exon Microarray Target Preparation, Array Hybridization and Data Analysis

Biotinylated sense-strand DNA targets were prepared using the Affymetrix GENECHIP® whole-transcript (WT) sense target labeling assay in accordance with manufacturer's directions, One microgram of total RNA from cells treated with chlorhexidine (n=3), clotrimazole (n=3), flunarizine (n=3), and DMSO (n=6) was used as an input for rRNA reduction with an Invitrogen RIBOMINUS™ transcriptome isolation kit in accordance with manufacturer's directions. The total resulting volume was used for the first round of amplification. Ten micrograms of the resulting cRNA was used to proceed to the second round of amplification. A hybridization cocktail including 5.5 pg of fragmented, end-labeled single-stranded DNA (ssDNA) was applied to GENECHIP® Human Exon 1.0 ST arrays. Hybridization was performed using F450-001 fluidics wash and stain script on an Affymetrix GENECHIP® Fluidics Station 450. Arrays were scanned using an Affymetrix GCS 3000 7G and GENECHIP® operating software (GCOS) to produce CEL intensity files.

Probe set intensities were calculated from the CEL files of the 15 samples by using the robust multiarray average (RMA) algorithm with default settings at both the gene level and the probe set level in PARTEK® Genomic Suite 6.4, using the core probe sets as defined by Affymetrix. Probe sets with a maximum RMA intensity of 3 across all samples were excluded to eliminate probe sets with low expression levels. Alternative splicing multiway analysis of variance (ANOVA) was applied using PARTEK® defaults with terms (probe set identification number and group), not only reflecting experimental conditions, but also allowing detection of alternative splicing events that differ between the treated samples and their appropriate controls, Step-up false discovery rates (FDR) were calculated, and genes with FDR values of <0.01 for differential expression or alternative splicing were considered. One-way ANOVA was also applied at the exon level to determine differential expression of exons. These data were used to generate heat maps by using SpotFire DecisionSite.

Microarray Data Accession Number

The CEL files were deposited in the NCBI Gene Expression Omnibus repository under accession number GSE19891.

The results of the experiments presented in this Example are now described.

Example 1

Rapid-Response for Discovery of Modulators Modulators of Splicing

In order to identify small molecules that regulate the splicing machinery or splicing-dependent processes, a reporter gene was generated in which the open reading frame (ORF) of firefly (*Photinus pyralis*) luciferase is interrupted by a chimeric intron with high splicing efficiency (FIG. 1A). In cases where the intron is not spliced out, several stop codon will be placed in frame of the luciferase ORF. In order to characterize the splicing reporters, cells were transfected with either intronless (Luc) or intron-containing (Luc I) luciferase reporters. Consistent with previous reports (Diem et al., 2007, Nat Struct Mol Biol 14:1173-1179; Nott et al., 2004, Genes Dev 18:210-222; Wiegand et al., 2003, Proc Natl Acad Sci USA 100:11327-11332), splicing conferred advantage to gene expression as equal amounts of transfected DNA constructs generated 2-3 fold more light signal from Luc I compared to Luc (FIG. 1B).

Since splicing is an essential process in mammalian cells it was reasoned that small molecules which inhibit splicing might be highly toxic to cells. Thus, the time during which cells are exposed to small molecules should be minimal (<4 hours) so that no global toxic effects are observed, but long enough for the reporter to sense changes in splicing. For this to be feasible, the splicing reporter needs to be highly sensitive and fast-responding. To achieve this, the half-lives of both reporter protein and luciferase mRNA were shortened by introducing destabilizing sequences (DS) to the C-terminus of the protein (protein DS:CL1 and PEST) as well as five consecutive AUUU elements added to the 3'UTR (RNA DS ARE) (FIG. 1A). It was confirmed that these elements confer fast response by treatment of Luc or Luc I transfected cells with either Cycloheximide or Actinomycin D. As depicted in FIG. 1C, four hour treatment with Cycloheximide, which blocks protein synthesis, lead to loss of 90% of the luciferase signal, indicating that the reporter protein does not accumulate in cells and it is highly sensitive to inhibitors of gene expression. Blocking transcription with Actinomycin D for the same time period caused 60% reduction in the signal, suggesting that the mRNA has a half-life of less than 4 hours. Importantly, both reporters had similar responses to regulation of gene expression, eliminating the need to adjust for potentially differential stability conferred by splicing of the Luc I construct. It was concluded that the reporter should be able to pick up changes in splicing, especially inhibition within four hours of drug administration to cells. All further analyses of the luciferase reporter was performed within that time frame.

Example 2

High-Throughput Screen for Modulators of Splicing

HeLa cell lines harboring the Luc or Luc I luciferase reporter were generated. Analysis of RNA extracted from these cells revealed that the majority of detectable Luc I mRNA from the stable lines is spliced (data not shown). To identify small molecule modulators of splicing, a high-throughput screen utilizing these cell lines was performed. The strategy of the screen is summarized in FIG. 2A. Shown in FIG. 2B is a representative plate treated with DMSO. Analysis of this plate shows high signal to noise ratio, a coefficient of variation (CV) of 11-15%, and a Z' factor of 0.5-0.6. These data indicate that this cell-based assay is highly reliable and amenable for high-throughput screening.

A collection of >23,000 chemically and functionally diverse compounds assembled from commercial sources was first screened using cells expressing Luc I. The first round of the screen generated 250 compounds that show an effect more than 3 times the standard deviation on Luc I cells when compared to the DMSO treated wells in the same plate. In order to eliminate compounds that modulate firefly luciferase enzymatic activity as well as compounds that inhibit transcription or translation, the same compounds were counter-screened on the intronless luciferase containing cell line Luc. A large fraction of compounds modulated Luc in the same manner to Luc I cells, indicating that they are either regulators of splicing-independent processes in gene expression, or modulators of firefly luciferase enzyme. Nevertheless, several compounds passed this counter-screen and were further analyzed.

Example 3

Identification and Characterization of Splicing Modulators

Additional compounds that showed an intron-dependent effect were studied further (Table 3 below). Three of these, clotrimazole {1-[(2-chlorophenyl)-di(phenyl)methyl]imidazole}, flunarizine {1-[bis(4-fluorophenyl)methyl]-4-[(E)-3-phenylprop-2-enyl]piperazine}, and chlorhexidine {(1E)-2-[6-[[amino-[[amino-(4-chloroanilino)methylidene]amino]methylidene]amino]hexyl]-1-[amino-(4-chloro-anilino)methylidene]guanidine}, are compounds in wide clinical use and have not previously been shown to affect splicing.

The original screen and the counter-screen were performed at a compound concentration of 20 μM and showed a marked difference between Luc and Luc I expression upon treatment with clotrimazole, flunarizine and chlorhexidine. Dose response curves were generated for the three compounds. While clotrimazole and flunarizine showed a dose-dependent inhibition of Luc I with IC50s between 40-50 μM, chlorhexidine showed a modest decrease in Luc I signal at concentrations up to 20 μM (FIG. 3), Higher concentrations of chlorhexidine were toxic at 4 hour treatment (data not shown). In order to verify that the change in Luc I signal was due to splicing modulation, real-time PCR was used to measure the levels of spliced Luc mRNA in cells treated with the three compounds at IC50. Data presented in FIG. 3 corroborate the luciferase assay showing that both clotrimazole and flunarizine cause reduction in spliced Luc I mRNA levels while chlorhexidine has only a modest effect on constitutive splicing. The spliced mRNA measurements were normalized to those of intronless Luc in order to eliminate effects on transcription or RNA stability.

Example 4

Compounds Modulate Splicing of Endogenous Genes In Vivo

To determine the effect of the compounds on splicing of endogenous genes, constitutive and alternative splicing patterns of several genes were analyzed by RT-PCR. Interestingly, none of the compounds inhibited every splicing event; rather, each compound showed a unique pattern of inhibition and induced distinct alternative splicing For example, both clotrimazole and flunarizine inhibited splicing of coilin intron 2, whereas chlorhexidine, which had no effect on this intron, modulated the splicing of several alternatively spliced exons, including SR protein-regulated RON exon 11 and caspase 9 (FIG. 4A). Real time PCR was performed to obtain a quantitative analysis of the differential effects of these compounds. Detailed real-time PCR for spliced and unspliced mRNAs of several major (U2-dependent) and minor (U12-dependent) introns was performed. As depicted in FIG. 4B, splicing of both major (coilin and ILK) and minor (CCDC56 and IK) introns was strongly inhibited by clotrimazole and flunarizine, albeit to different extents, while chlorhexidine only slightly inhibited the splicing of ILF2 intron 4 and IK intron 14 (FIG. 4B). The analysis was further extended to more than about 30 constitutively spliced introns that had a wide range of sizes and have not previously been shown to be regulated (FIG. 4C). These data indicated that clotrimazole and flunarizine are not general splicing inhibitors. Instead, each inhibited a subset of these introns, whereas chlorhexidine inhibited a smaller and distinct set of constitutively spliced introns (FIG. 4C), suggesting that these compounds regulate splicing by different mechanisms. Bioinformatic analysis of the affected introns did not show distinctive features, such as splice site strength or common motifs. Nevertheless, these data uncover an unexpected differential regulation of constitutively spliced introns in cells.

Example 5

Chlorhexidine Modulates SR Protein-Dependent Splicing

Figure 5A:
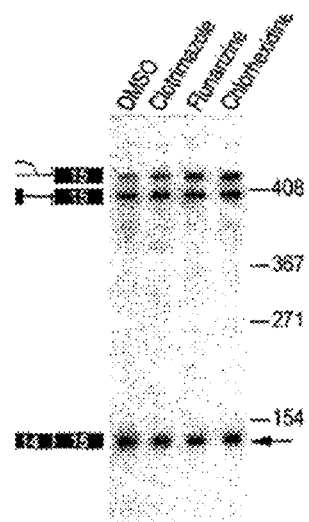
FIG. 5A and FIG. 5B, is a series of images depicting in vitro effects of splicing modulators.
Figure 5B:
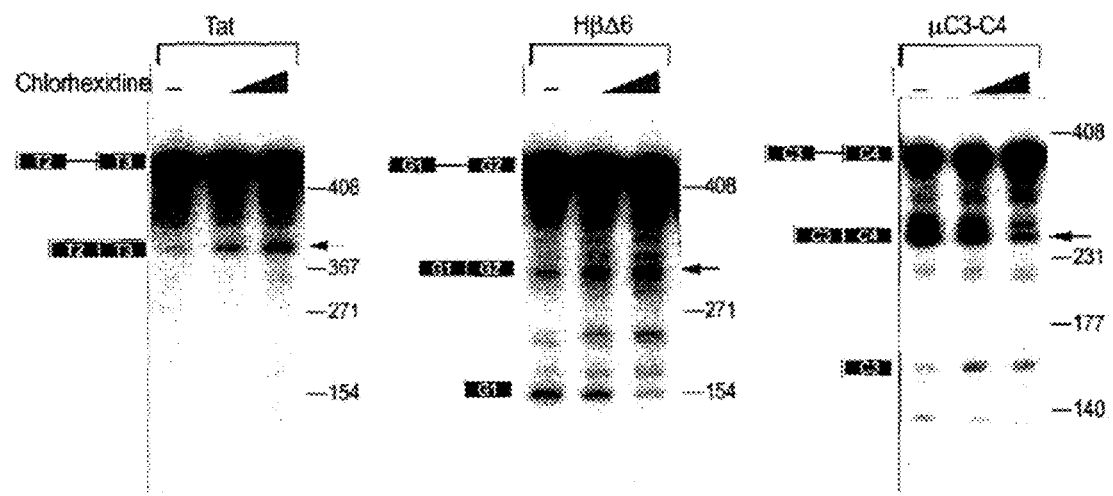

To further the understanding of the role of the compounds identified using the present method in regulating constitutive and SR-dependent splicing, constitutive pre-mRNA constructs as well as several SR protein-dependent pre-mRNAs were used for in vitro splicing reactions, CδC pre-mRNA splicing is not dependent on SR protein in Hela nuclear extracts. None of the compounds showed any effect on constitutive splicing of CδC pre-mRNA in vitro (FIG. 5A), suggesting that rather than targeting the spliceosome, they may be targeting cellular pathways that regulate a subset of genes in vivo. On the other hand, chlorhexidine modulated the in vitro splicing of the three SR protein-regulated pre-mRNAs that were tested (Tat, μC3-C4, and HβΔ6), suggesting that it can modulate SR protein-regulated splicing both in vitro and in vivo (FIG. 5B and FIG. 4A). Given the complexity of SR protein binding and regulation of these pre-mRNAs and the fact that chlorhexidine did not affect the phosphorylation of all SR proteins to the same level, it is impossible to predict the outcome of chlorhexidine treatment. In this case, chlorhexidine increased splicing efficiency from SR protein dependent pre-mRNAs. This could be explained in light of previous data showing that SC35 can bind to an exonic splicing silencer and repress splicing of Tat2-3, While SC35 has not been shown to act in the same manner on HβΔ6, several reports have pointed to a negative role for various SR proteins in splicing (Gallego et al., 1997, EMBO J 16:1772-1784, McNally et al., 1996 J Virol 70:1163-1172, Kanopka et al., 1996, Nature 381:535-538, Wang and Manley, 1995, RNA 1:335-346), indicating that any combination of SR proteins can negatively regulate splicing of these pre-mRNAs, and treatment with chlorhexidine could disrupt the balance of these SR proteins resulting in the release of suppressor SR proteins.

Example 6

Chlorhexidine Inhibits SR Protein Phosphorylation In Vivo

Figure 6A:
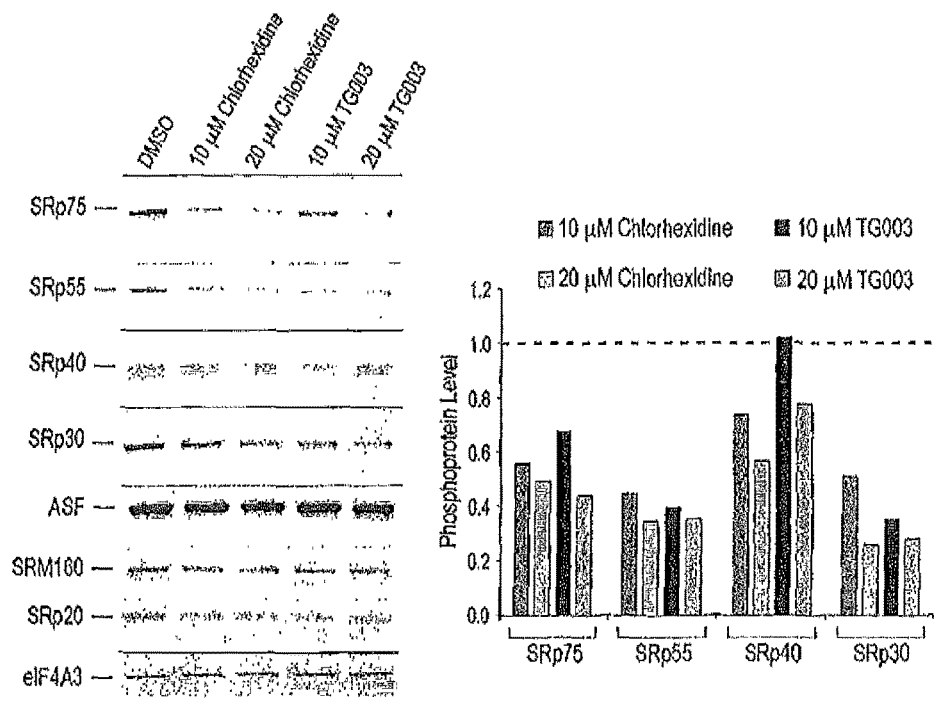
FIG. 6A and FIG. 6B, is a series of images depicting chlorhexidine inhibition of SR protein phosphorylation in vivo.
Figure 6B:
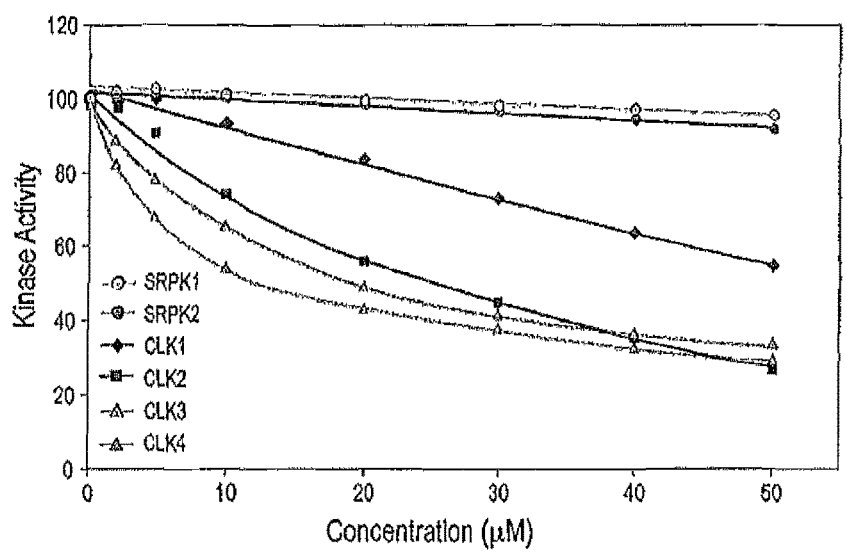

Chlorhexidine demonstrated a unique effect on SR-dependent splicing (FIG. 4). Its role in modulating SR protein phosphorylation, a hallmark of SR protein regulation, was investigated. Using a phospho-specific antibody against SR proteins (1H4) it was shown that chlorhexidine decreased the phosphorylation level of several SR proteins, including SRp75, SRp55, SRp40, and SRp30, at concentrations as low as 10 μM (FIG. 6A). These effects were comparable to those observed for TG003, a previously described regulator of SR protein phosphorylation (Muraki et al., 2004, J Biol Chem 279:24246-24254). Other SR and SR-like proteins, such as SF2/ASF, SRp20, and SRm160, were not significantly affected at these concentrations. As a control, other proteins involved in mRNA biogenesis were not affected (FIG. 6A).

Example 7

Chlorhexidine is a Specific Inhibitor of the Clk Family of SR Protein Kinases

Chlorhexidine has pronounced effects on SR-dependent splicing in vivo and in vitro, SR protein phosphorylation and localization. Therefore, its effects were tested on several kinases that are known to target SR proteins. As demonstrated herein, by using recombinant kinases and an SR-rich peptide derived from SF2/ASF, chlorhexidine has specific inhibitory activity against the Cdc2-like kinase (Clk) family of SR protein kinases. Whereas the other SR protein kinases (SRPK1 and SRPK2) as well as other unrelated kinases (ERK1 and JNK1) were not targeted by chlorhexidine (FIG. 7B). Moreover, chlorhexidine has selectivity for different members of the Clk family: Clk4 (IC50 10 μM), Clk3 (IC50 15 μM) and Clk2 (IC50 25 μM) over Clk1 (IC50>50 μM). Taken together, these results suggest a specific mechanism by which chlorhexidine inhibits Clks in cells, leading to the aberrant phosphorylation of a subset of SR proteins, which, in turn, results in the misregulation of alternative splicing.

Example 8

Differential Effects of the Compounds on Alternative Splicing

Figure 7:
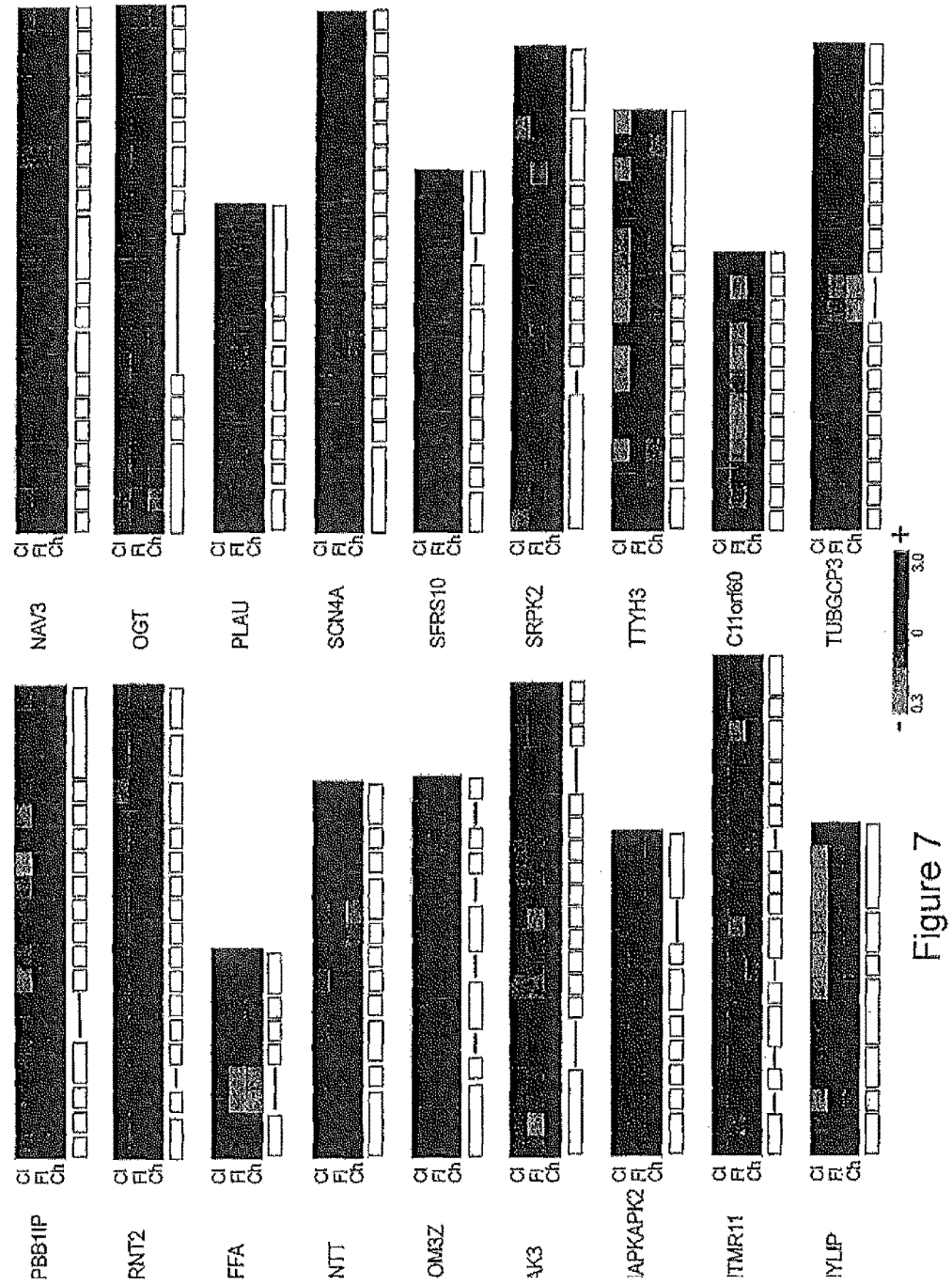
FIG. 7, is a series of heatmaps that depict the differential effects of splicing modulators on alternative splicing. Heat maps of representative transcripts from the exon array are shown, with the gene structure depicted below the heat map.
Figure 8:
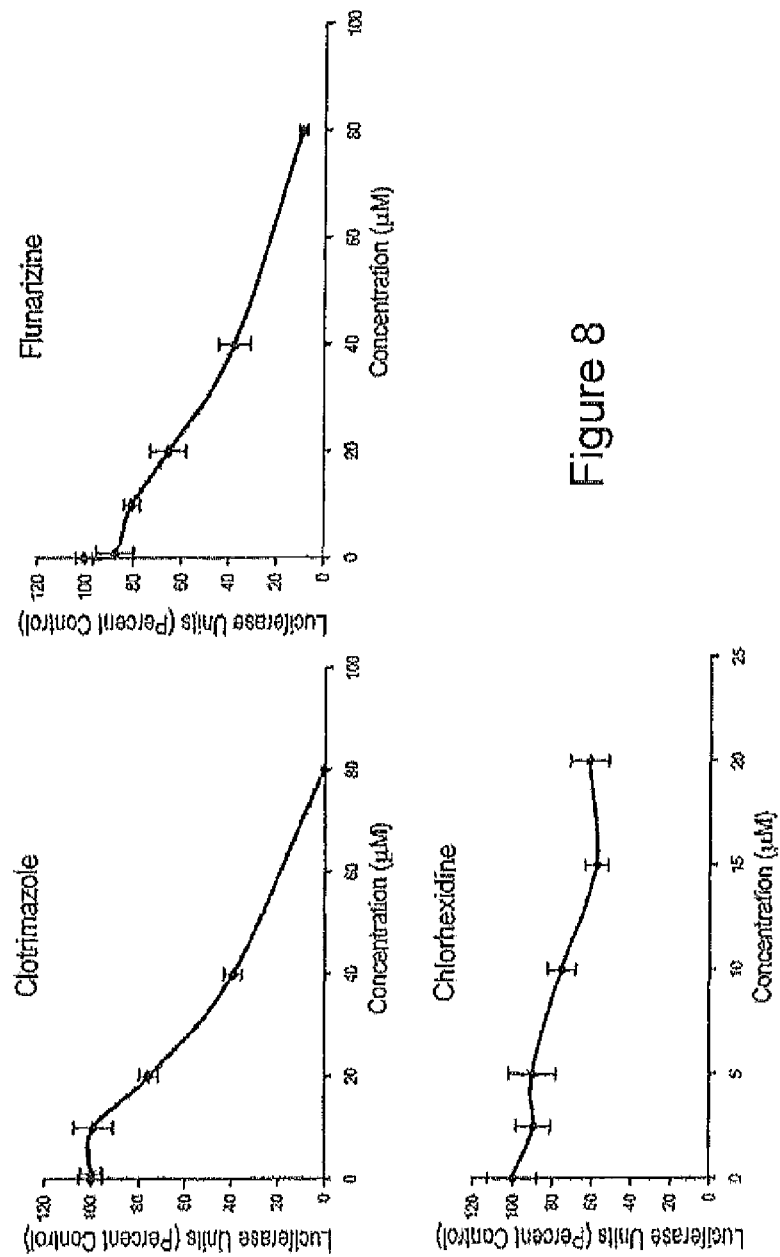
FIG. 8, a series of graphs, depicts dose responses for the splicing modulators. Ten thousand stably expressing cells were treated with DMSO or increasing concentrations of compounds in a 96 well plate for 4 hours, followed by a luciferase assay.
Figure 10A:
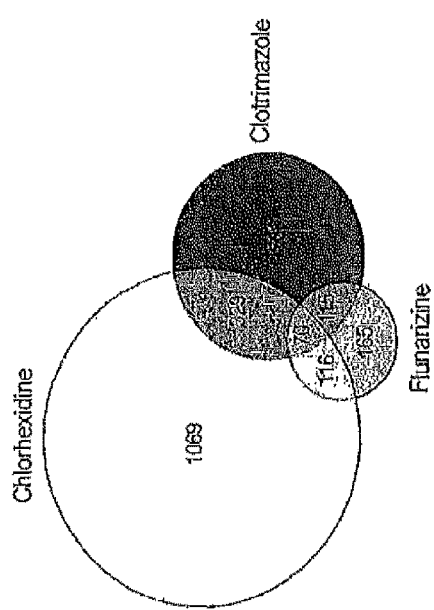
FIG. 10A and FIG. 10B, depicts the regulation of alternative splicing by three compounds.
Figure 10B:
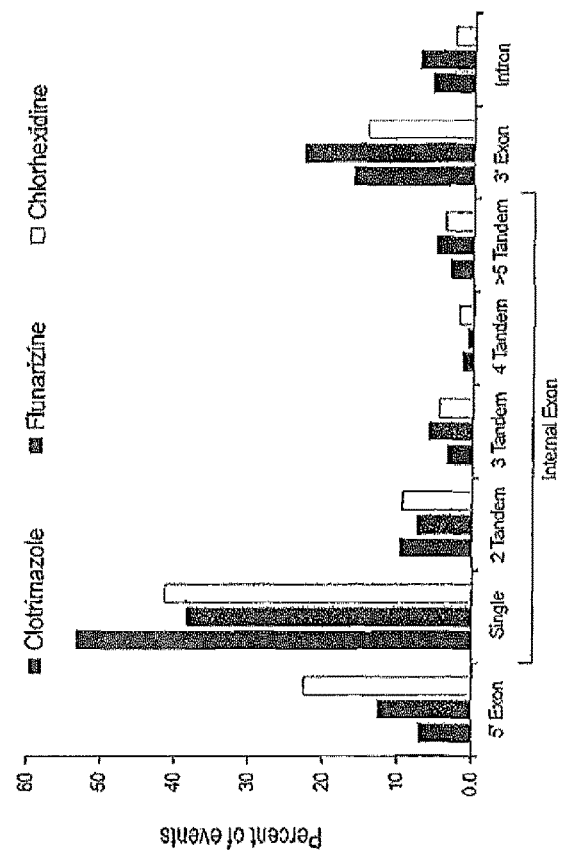

Given the effect of chlorhexidine on several alternatively spliced exons, clotrimazole, flunarizine and chlorhexide were assessed on splicing at a genome wide level. RNAs processed from cells treated with clotrimazole (40 µM), flunarizine (40 µM), and chlorhexidine (10 µM) were analyzed by exon arrays. For chlorhexidine, a large number of alternative splicing changes were observed (1,444 transcripts at FDR values of <0.01), compared to only 191 genes affected at the whole-transcript level, namely, at transcriptional or mRNA stability levels, indicating high selectivity of chlorhexidine for alternative splicing regulation (see Table 2). Clotrimazole and flunarizine were found to cause fewer alternative splicing changes when the same statistical cutoff was used (874 and 326 genes, respectively). Confirmation of a select number of the affected transcripts is presented in FIG. 9, and the overlap among these transcripts and the breakdown of the splicing alterations are depicted in FIG. 10. It is noted that transcripts that were affected by at least two of the compounds frequently showed different profiles at the exon level (FIG. 7). For example, some exons were increased or decreased in all three treatments (DOM3Z, MYLIP, and TTYH3). Others were affected by two of the three compounds (ARNT2, SCN4A, DNTT, and NAV3), whereas some showed opposing effects in different treatments (APBB1IP, JAK3, MTMR11, C11orf60, PLAU, and SRPK2). In addition, some transcripts with intronic probes showed unique effects for each of the three compounds (DFFA, OGT, MTMR11, MAPKAPK2, TUBGCP3, and SFRS10). Thus, clotrimazole, flunarizine, and chlorhexidine have differential effects on constitutively spliced introns and on alternative splicing in cells.

TABLE 2

Summary of the exon array for splicing inhibitors
(all analyses were performed with FDR <0.01)

|  | Total Transcripts Analyzed | Transcript level changes | Alternative splicing changes |
|---|---|---|---|
| Chlorhexidine | 17867 | 191 | 1444 |
| Clotrimazole | 17859 | <5 | 874 |
| Flunarizine | 17868 | <5 | 326 |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of identifying a candidate general or alternative splicing inhibitor of RNA splicing comprising a two step assay, said method comprising the steps of:
    a) a first screening step comprising assessing the effect of a candidate general or alternative splicing inhibitor on expression, function, or activity of a first reporter construct expressed by a first recombinant mammalian cell by exposing said candidate general or alternative splicing inhibitor to said first recombinant cell for less than 4 hours, said first reporter construct comprising an open reading frame (ORF) interrupted by a chimeric β-globin intron, wherein the chimeric β-globin intron comprises multiple internal stop codons, wherein protein translated from unspliced transcripts is truncated, further wherein said first reporter construct comprises a protein and RNA destabilizing sequence and has a half-life of less than 4 hours, wherein the candidate alternative splice inhibitor is selected for a subsequent counter screen when the candidate inhibits the expression, activity, or function of the reporter protein relative to control;
    b) after the first screening step, a second counter-screening step comprising assessing the effect of the selected candidate inhibitor from the first screen on the expression, function, or activity of a second reporter construct expressed by a second recombinant mammalian cell by exposing the selected candidate inhibitor from the first screen to said second recombinant cell for less than 4 hours, said second reporter construct comprising an intronless ORF, further wherein said second reporter construct comprises a protein and RNA destabilizing sequence and has a half-life of less than 4 hours, wherein when the selected candidate inhibitor has a different effect on the expression, function, or activity of the intronless reporter construct of the first screening step as compared to the intron containing reporter construct, then the selected candidate compound is identified as an inhibitor of constitutive or alternative splicing.

2. The method of claim 1, wherein said first reporter construct encodes luciferase.

3. The method of claim 2, wherein said intronless reporter construct is Luc.

4. The method of claim 2, wherein said intron-containing reporter construct is Luc I.

* * * * *